United States Patent
Hofstetter et al.

(10) Patent No.: US 10,866,188 B2
(45) Date of Patent: Dec. 15, 2020

(54) FINGERMARK LIFTING AND VISUALIZATION DEVICE AND METHODS OF USE THEREOF

(71) Applicant: Board of Trustees of Northern Illinois University, DeKalb, IL (US)

(72) Inventors: Oliver D. Hofstetter, DeKalb, IL (US); Andrei Mlakar, Glenview, IL (US); Claude Roux, Sydney (AU); Xanthe Spindler, Sydney (AU); Chris Lennard, Richmond (AU)

(73) Assignee: Board of Trustees of Northern Illinois University, DeKalb, IL (US)

( * ) Notice: Subject to any disclaimer, the term of this patent is extended or adjusted under 35 U.S.C. 154(b) by 131 days.

(21) Appl. No.: 15/945,142

(22) Filed: Apr. 4, 2018

(65) Prior Publication Data
US 2019/0310195 A1    Oct. 10, 2019

(51) Int. Cl.
| | |
|---|---|
| *G01N 21/64* | (2006.01) |
| *G01N 21/77* | (2006.01) |
| *G01N 21/78* | (2006.01) |
| *G01N 21/84* | (2006.01) |
| *G01N 31/22* | (2006.01) |
| *A61B 5/1172* | (2016.01) |

(52) U.S. Cl.
CPC ......... *G01N 21/6447* (2013.01); *G01N 21/77* (2013.01); *G01N 21/84* (2013.01); *G01N 31/22* (2013.01); *A61B 5/1172* (2013.01); *G01N 31/221* (2013.01)

(58) Field of Classification Search
CPC .. A61B 5/1172; G01N 21/6447; G01N 21/77; G01N 21/84; G01N 31/22; G01N 31/221
See application file for complete search history.

(56) References Cited

U.S. PATENT DOCUMENTS

| | | | | | |
|---|---|---|---|---|---|
| 6,127,189 | A | * | 10/2000 | Joullie | C07C 45/516 |
| | | | | | 422/504 |
| 2008/0057533 | A1 | * | 3/2008 | Martin | C12Q 1/04 |
| | | | | | 435/34 |
| 2008/0136159 | A1 | | 6/2008 | Zarate | |
| 2010/0040765 | A1 | | 2/2010 | Zarate | |
| 2010/0047433 | A1 | | 2/2010 | Shimoda et al. | |

(Continued)

FOREIGN PATENT DOCUMENTS

| | | |
|---|---|---|
| CN | 101308061 | 6/2011 |
| CN | 103431867 | 12/2013 |

(Continued)

OTHER PUBLICATIONS

Tahtouh, M. et al., "The application of infrared chemical imaging to the detection and enhancement of latent fingerprints: Method optimization and further findings", Journal of Forensic Sciences, vol. 52, pp. 1089-1102, (2007). (Year: 2007).*

(Continued)

*Primary Examiner* — Jennifer Wecker
(74) *Attorney, Agent, or Firm* — Evan Law Group LLC

(57) ABSTRACT

A fingermark lifting and visualization device includes a carrier and an indicator. The carrier has a lifting surface. The indicator is immobilized on the lifting surface. The indicator changes color or changes in fluorescence in the visible spectrum in response to contact with a glandular secretion.

30 Claims, 20 Drawing Sheets

(56) References Cited

U.S. PATENT DOCUMENTS

| | | | | |
|---|---|---|---|---|
| 2010/0136208 | A1* | 6/2010 | Zarate | B42D 15/00 427/1 |
| 2010/0310755 | A1 | 12/2010 | Attar | |
| 2011/0104815 | A1 | 5/2011 | Cole-Hamilton et al. | |
| 2011/0250626 | A1* | 10/2011 | Williams | C12Q 1/61 435/18 |
| 2014/0350127 | A1* | 11/2014 | Cano | A61K 47/34 514/772.7 |
| 2017/0281053 | A1* | 10/2017 | Kelarakis | A61B 5/117 |

FOREIGN PATENT DOCUMENTS

| | | |
|---|---|---|
| CN | 106248647 | 12/2016 |
| CN | 105411599 | 3/2019 |
| CN | 106596482 | 4/2019 |
| DE | 3245204 | 6/1983 |
| WO | 2019/195459 | 10/2019 |

OTHER PUBLICATIONS

Hofstetter, O. et al., "Next-generation fingermark lifters with instant visualization capability", Pittcon 2020, Pittcon and the Pittsburgh Conference on Analytical Chemistry and Applied Spectroscopy, 1 page, Mar. 2, 2020. Abstract Only.

Mlakar, A. et al., "On-the-spot reactive lifters for field-based latent fingermark detection", International Fingerprint Research Group Biennial Meeting, Sheffield, UK, 1 page, Jun. 28, 2019. Abstract Only.

"Fingerprint", available online at en.wikipedia.org/Fingerprint (Oct. 1, 2017).

"Fingerprint powder", available online at en.wikipedia.org/Fingerprint_powder (Oct. 17, 2017).

Sodhi, G.S. et al., "Physical developer method for detection of latent fingerprints: a review", Egyptian Journal of Forensic Sciences, vol. 6, pp. 44-47 (2016).

"Processing guide for developing latent prints", U.S. Department of Justice Federal Bureau of Investigation (2000).

Product Information "Gelatin lifters", BVDA International, pp. 1-6, available online at www.bvda.com/EN/download/en_gellifters.pdf (accessed on Nov. 13, 2017).

"Method for fingerprint identification", Interpol European Expert Group on Fingerprint Identification, pp. 1-27, (2006).

International Fingerprint Research Group, "Guidelines for the assessment of fingermark detection techniques", Journal of Forensic Identification, vol. 64, No. 2, pp. 174-200 (2014).

"What is Zar-Pro?", available online at www.zar-pro.com, 2010.

Almog, J. et al., "Aminoninhydrins: fingerprint reagents with direct fluorogenic activity—preliminary studies", Journal of Forensic Sciences, vol. 36, pp. 104-110 (1991).

Urano, Y. et al., "Selective molecular imaging of viable cancer cells with pH-activatable fluorescence probes", Nature Medicine, vol. 15, pp. 104-109 (2009).

Tahtouh, M. et al., "The detection and enhancement of latent fingermarks using infrared chemical imaging," Journal of Forensic Sciences, vol. 50, No. 1, pp. JFS2004213-9 (2005).

Wood, M. et al., "Visualization of latent fingermarks using an aptamer-based reagent", Angewandte Chemie International Edition, vol. 51, pp. 12272-12274 (2012).

Worley, C.G. et al., "Detection of visible and latent fingerprints using micro-X-ray fluorescence elemental imaging", Journal of Forensic Sciences, vol. 51, pp. 57-63 (2006).

Dilag, J. et al., "Cadmium sulfide quantum dot/chitosan nanocomposites for latent fingermark detection", Forensic Science International, vol. 187, No. 1-3, pp. 97-102 (2009).

Wiesner, S. et al., "Chemical development of latent fingerprints: 1,2-indanedione has come of age," Journal of Forensic Sciences, vol. 46, No. 5, pp. 1082-1084 (2001).

Crane, N.J. et al., "Infrared spectroscopic imaging for noninvasive detection of latent fingerprints", Journal of Forensic Sciences, vol. 52, pp. 48-53 (2007).

Park, D-H. et al., "Hydrochromic approaches to mapping human sweat pores", Accounts of Chemical Research, vol. 49, No. 6, pp. 1211-1222 (2016).

van Dam, A. et al., "The compatibility of fingerprint visualization techniques with immunolabeling", Journal of Forensic Sciences, vol. 58, pp. 999-1002 (2013).

Wu, P. et al., "Dual-emitting quantum dot nanohybrid for imaging of latent fingerprints: simultaneous identification of individuals and traffic light-type visualization of TNT", Chemical Science, vol. 6, pp. 4445-4450 (2015).

Ma, R. et al., "Fingermark detection on non-porous and semi-porous surfaces using YVO4:Er,Yb luminescent upconverting particles", Forensic Science International vol. 217, pp. e23-e26 (2012).

Chadwick, S. et al., "Styryl dye coated metal oxide powders for the detection of latent fingermarks on non-porous surfaces", Forensic Science International, vol. 219, pp. 208-214 (2012).

Moret, S., "Application de nanoparticules luminescentes pour la detection de traces papillaires" Doctoral Thesis, University of Lausanne (2013). English Abstract.

Tahtouh, M. et al., "The application of infrared chemical imaging to the detection and enhancement of latent fingerprints: Method optimization and further findings", Journal of Forensic Sciences, vol. 52, pp. 1089-1102, (2007).

Wilkinson, D., "A one-step fluorescent detection method for lipid fingerprints; Eu(TTA)3•2TOPO", Forensic Science International, vol. 99, pp. 5-23 (1999).

Jaber, N. et al., "Visualization of latent fingermarks by nanotechnology: Reversed development on paper—A remedy to the variation in sweat composition", Angewandte Chemie International Edition, vol. 51, pp. 12224-12227 (2012).

Kent, T., "Standardizing protocols for fingerprint reagent testing", Journal of Forensic Identification, vol. 60, pp. 371-379 (2010). Abstract Only.

Wiesner, S. et al., "Lifting bloody footwear impressions using alginate casts followed by chemical enhancement", Journal of Forensic Sciences, vol. 58, pp. 782-788 (2013).

Horvath, D., "Evaluation of alginate casting material for the lifting of latent and blood contaminated fingermarks from various surfaces", Master of Science Thesis, University of Technology Sydney (2014).

Theeuwen, A.B.E. et al., "Enhancement of footwear impressions in blood", Forensic Science International, vol. 95, pp. 133-151 (1998).

Farrugia, K.J. et al., "A Comparison of enhancement techniques for footwear impressions on dark and patterned fabrics", Journal of Forensic Sciences, vol. 58, pp. 1472-1485 (2013).

Munro, M. et al., "A preliminary investigation into the use of alginates for the lifting and enhancement of fingermarks in blood", Science and Justice, vol. 54, pp. 185-191 (2014).

Yang, R. et al., "Studies on the development of latent fingerprints by the method of solid medium ninhydrin", Forensic Science International, vol. 242, pp. 123-126 (2014).

Zarate, J. et al., "A fluorogenic method for lifting, enhancing, and preserving bloody impression evidence", Journal of Forensic Identification, vol. 61, pp. 260-280 (2011).

Becue, A., "Emerging fields in fingermark (meta)detection—A critical review", Analytical Methods, vol. 8, pp. 7983-8003 (2016).

Spindler, X. et al., "Enhancement of latent fingermarks on non-porous surfaces using anti-L-amino acid antibodies conjugated to gold nanoparticles", Chemical Communications, vol. 47, pp. 5602-5604 (2011).

Ramotowski, R.S., "Composition of latent print residue", Advances in Fingerprint Technology, 2nd ed., Chapter 3; CRC Press, Boca Raton, FL, pp. 63-104, (2001).

Kaiser, D. et al., "Hydrogen ion and electrolyte excretion of the single human sweat gland", Pflügers Archiv—European Journal of Physiology, vol. 349, pp. 63-72 (1974).

Kaiser, D. et al., "Diminished excretion of bicarbonate from the single sweat gland of patients with cystic fibrosis of the pancreas", European Journal of Clinical Investigation, vol. 4, pp. 261-265 (1974).

(56) References Cited

OTHER PUBLICATIONS

Curto, V.F. et al., "Concept and development of an autonomous wearable micro-fluidic platform for real time pH sweat analysis", Sensors and Actuators B—Chemical, vol. 175, pp. 263-270 (2012).
Neupert, M., "Lackmus", Römpp Lexikon Chemie, available online at www.chemeurope.com/en/encyclopedia/Litmus_test_%28chemistry%29.html (2013).
Bamfield, P., "Chromic phenomena: The technological applications of colour chemistry", The Royal Society of Chemistry, Cambridge, UK, p. 41 (2010).
Williams, A. et al., "Carbodiimide chemistry: Recent advances", Chemical Reviews, vol. 81, pp. 589-636 (1981).
Hermanson, G.T., "Bioconjugate chemistry", 3rd ed., Elsevier, Amsterdam pp. 237-238, 246-248 (2013).
Han, J. et al., "Fluorescent indicators for intracellular pH", Chemical Reviews, vol. 110, pp. 2709-2728 (2010).
"LysoTracker and LysoSensor Probes", Molecular Probes by life technologies, available online at tools.thermofisher.com/content/sfs/manuals/mp07525.pdf (2013).
"pHrodo Indicators for pH Determination", ThermoFisher Scientific, available online at www.thermofisher.com/us/en/home/brands/molecular-probes/key-molecular-probes-products/phrodo-indicators.html (accessed on Jan. 5, 2018).
Galindo, F. et al., "Synthetic macrocyclic peptidomimetics as tunable pH probes for the fluorescence imaging of acidic organelles in live cells", Angewandte Chemie International Edition, vol. 44, pp. 6504-6508 (2005).
Werner, T. et al., "Novel optical pH-sensor based on a boradiaza-indacene derivative", Fresenius Journal of Analytical Chemistry, vol. 359, pp. 150-154 (1997).
Yogo, T. et al., "Selective photoinactivation of protein function through environment-sensitive switching of singlet oxygen generation by photosensitizer", Proceedings of the National Academy of Sciences of the United States of America, vol. 105, pp. 28-32 (2008).
Xiong, H. et al., "Activatable water-soluble probes enhance tumor imaging by responding to dysregulated pH and exhibiting high tumor-to-liver fluorescence emission contrast", Bioconjugate Chemistry, vol. 27, pp. 1737-1744 (2016).
Liappis, N. et al., "The trace amino acid pattern in human eccrine sweat", Clinica Chimica Acta, vol. 48, pp. 233-236 (1973).
Liappis, N. et al., "Quantitative study of free amino acids in human eccrine sweat excreted from the forearms of healthy trained and untrained men during exercise", European Journal of Applied Physiology, vol. 42, pp. 227-234 (1979).
Odén, S. et al., "Detection of fingerprints by the ninhydrin reaction", Nature, vol. 173, pp. 449-450 (1954).
Yamashita, B. et al., "Latent print development", The fingerprint sourcebook, Chapter 7, National Institute of Justice, Washington, DC (2011).
Ramotowski, R.S., "Amino acid reagents", Lee and Gaensslen's Advances in fingerprint technology, 3rd ed., Chapter 2, CRC Press, Boca Raton, FL, pp. 17-53, (2013).
Hansen, D.B et al., "The development of novel ninhydrin analogues", Chemical Society Reviews, vol. 34, pp. 408-417 (2005).
Hark, R.R. et al., "Synthetic studies of novel ninhydrin analogs", Canadian Journal of Chemistry, vol. 79, pp. 1632-1654 (2001).
Hark, R.R., "Synthesis of ninhydrin analogues", Ph.D. Dissertation, University of Pennsylvania, pp. 1-614, (1996).
Ziarani, G.M. et al., "Ninhydrin in synthesis of heterocyclic compounds", ARKIVOC, vol. vi, pp. 1-139 (2015).
Regitz, R., "Reactivity towards acids", Diazo compounds, Chapter 3, Elsevier, Amsterdam, pp. 96-165, (1986).
National Research Council, "Strengthening forensic science in the United States: A path forward", National Academies Press, Washington, DC, pp. 1-352, (2009).
Pollanen, M.S. et al., "Forensic science in Canada", University of Toronto Hart House Report, pp. 1-113, (2012).
Mnookin, J.L. et al., "The need for a research culture in the forensic sciences", UCLA Law Review, vol. 58, pp. 725-779, (2011).
Hofstetter, O. et al., "Chiral Discrimination Using an Immunosensor", Nature Biotechnology, vol. 17, pp. 371-374 (1999).
Kassa, T. et al., "Antibody-based multiplex analysis of structurally closely related chiral molecules", Analyst, vol. 136, pp. 1113-1115 (2011).
Tsourkas, A. et al., "Magnetic relaxation switch immunosensors detect enantiomeric impurities", Angewandte Chemie International Edition, vol. 43, pp. 2395-2399 (2004).
Dutta, P. et al., "Enantioselective sensors based on antibody-mediated nanomechanics", Analytical Chemistry, vol. 75, pp. 2342-2348 (2003).
Quinn, S., "NIU chemistry professor gets $628,000 grant to develop new method of lifting fingerprints", NIU Today, available online at www.niutoday.info/2018/05/21/niu-chemistry-professor-gets-628000-grant-to-develop-new-method-of-lifting-fingerprints/ (May 21, 2018).
Hofstetter, O. et al., "Direct binding of low molecular weight haptens to ELISA plates", Journal of Immunological Methods, vol. 210, pp. 89-92 (1997).
"NIJ Award Detail: Development of next-generation fingermark lifters and on-the-spot visualization devices", U.S. Department of Justice, Office of Justice Programs, National Institute of Justice, available online at www.nij.gov/ funding/awards/pages/award-detail.aspx?award=2017-DN-BX-0167 (accessed on Oct. 23, 2017).
International Search Report and Written Opinion dated Jul. 26, 2019 for PCT application No. PCT/US2019/025630.
Moret, S. et al., "Cadmium-free quantum dots in aqueous solution: Potential for fingermark detection, synthesis and an application to the detection of fingermarks in blood on non-porous surfaces", Forensic Science International, vol. 224, pp. 101-110, (2013).
Becue, A. et al., "Use of quantum dots in aqueous solution to detect blood fingermarks on non-porous surfaces", Forensic Science International, vol. 191, pp. 36-41, (2009).

\* cited by examiner

FINGERMARK LIFTING AND VISUALIZATION DEVICE AND METHODS OF USE THEREOF

BACKGROUND

The epidermis of the palms of the hands and soles of the feet includes raised portions referred to as friction ridges, epidermal ridges or papillary ridges. Friction ridges contain features known as minutiae and patterned ridge formations such as arches, loops and whorls. The specific pattern of friction ridges is generally assumed to be unique to each individual and remains relatively unchanged over time. Friction ridges maintain their patterns under varying amounts of pressure and when the skin is stretched. This combination of extreme polymorphism of the papillary pattern and consistency has led to friction ridges being frequently used as a form of biometric identification.

Fingermarks are created when the friction ridges of a finger contact a substrate. Any material that is present on the friction ridges may be transferred to the substrate. Some substances, such as blood, paint, oil, grease or ink, will leave a visible residue on the substrate. Other substances, such as secretions from eccrine, apocrine or sebaceous glands found on the friction ridges, are invisible on the substrate. Visible and invisible fingermarks are also known as patent and latent fingermarks, respectively. Fingermarks that are collected in a standardized or controlled manner (as opposed to marks left in the course of activities) are typically called fingerprints.

Detecting fingermarks and preserving them as evidence are important forensic science techniques for law enforcement. Visible fingermarks are readily detected and may be easily preserved as evidence by photographing the fingermarks on the substrate. Invisible fingermarks require modification to make them visible for detection, such as treatment with a developer. A developer is a substance that adheres to a fingermark to provide a visible contrast between the fingermark and the substrate on which it is found. Developers are often provided as powders, such as colored powders, metallic powders or fluorescent powders, or liquids, such as particles in solution, ninhydrin solutions or silver nitrate solutions. An invisible fingermark that has been developed may then be preserved as evidence by photographing the developed fingermark on the substrate.

A developed fingermark may also be preserved as evidence by transferring it from its original substrate using a fingermark lifter. A fingermark lifter may be a specialized device, such as a gel lifter (a card with gelatin on its surface), or may be a clear adhesive substance, such as fingermark lifting tape or packing tape. The developed and lifted fingermark may then be protected by a clear film and/or transferred to a surface that may be removed from the crime scene, such as a backing card. The backing card with the developed and lifted fingermark may be used as evidence or may be preserved as evidence by being photographed.

In addition to detecting fingermarks at a crime scene, fingermarks may be detected and visualized in a forensic laboratory. Substrates bearing fingermarks that are easily transportable may be removed from a crime scene for additional processing. Alternatively, a fingermark may be lifted from a substrate for off-site development and visualization. Forensic laboratories typically have a number of advanced development tools for detecting fingermarks, such as cyanoacrylate fuming chambers and lasers. More complex detection techniques, such as vacuum metal deposition or FTIR hyperspectral imaging, have been developed, but the equipment required for these techniques is often not available to operational forensic laboratories.

The performance of a fingermark detection device or technique may be evaluated by examining the quality of the visualized fingermark it produces. The Interpol European Expert Group on Fingerprint Identification requires a fingermark detection device to be capable of clear visualization of at least 12 points in a fingermark to be considered safe for identification purposes ("Method for fingerprint identification", Interpol European Expert Group on Fingerprint Identification (2006)). Visualized fingermarks may also be evaluated according to grading schemes developed by the Centre for Applied Science & Technology (CAST) and/or the University of Lausanne (UNIL). The CAST grading scheme grades visualized fingermarks on a 0-4 point scale based on the amount of detail visualized as shown in Table 1 below:

TABLE 1

| CAST fingermark grading scheme | |
| --- | --- |
| Grade | Detail Visualized |
| 0 | No evidence of a fingermark |
| 1 | Some evidence of a fingermark |
| 2 | Less than ⅓ clear ridge detail |
| 3 | Between ⅓ and ⅔ clear ridge detail |
| 4 | Over ⅔ clear ridge detail |

The UNIL assessment scale assigns visualized fingermarks a symbol of −, ± or + based on the amount of detail visualized as shown in Table 2 below:

TABLE 2

| UNIL fingermark assessment scale | |
| --- | --- |
| Symbol | Detail Visualized |
| − | No visible reaction between the reagent and the ridges |
| ± | Ridges that are slightly visible but not sufficient to perform an analysis in terms of minutiae positioning |
| + | Clearly visible ridges with sufficient quality to see minutiae |

The International Fingerprint Research Group recommends that a fingermark lifting device be capable of visualizing a fingermark with a CAST grade of at least 2 and a UNIL assessment of at least ± (International Fingerprint Research Group, "Guidelines for the assessment of fingermark detection techniques", Journal of Forensic Identification, Vol. 64, No. 2, pp. 174-200 (2014)).

In addition to the quality of the visualized fingermark produced, fingermark lifting devices may also be evaluated based on the time involved in using the device. A fingermark detection device should be capable of visualizing an invisible fingermark rapidly after contacting glandular secretions. A fingermark detection device also should display a visualized fingermark for a sufficient amount of time to allow forensic scientists to photograph the visualized print.

SUMMARY

In a first aspect, the invention is a fingermark lifting and visualization device comprising a carrier having a lifting surface and an indicator, immobilized on the lifting surface. The indicator changes color or changes in fluorescence in the visible spectrum in response to contact with a glandular secretion. The device passes the fingermark point test, the basic visualization test, the basic contact time test and the basic stability test.

In a second aspect, the invention is a fingermark lifting and visualization device comprising a carrier having a lifting surface and an indicator, immobilized on the lifting surface. The carrier comprises a polymer selected from the group consisting of positively charged nylon, nylon, and polyvinylidene fluoride (PVDF). The indicator comprises a pH-sensitive substance. The pH of the indicator has been adjusted to be basic.

In a third aspect, the invention is a fingermark lifting and visualization device comprising a carrier having a lifting surface and an indicator, immobilized on the lifting surface. The carrier comprises a polymer selected from the group consisting of positively charged nylon, nylon, and polyvinylidene fluoride (PVDF). The indicator comprises an amine-reactive substance.

Definitions

The term "fingermark" means an impression left by friction ridges on a substrate.

The term "undeveloped fingermark" means a fingermark in its original state that has not been treated to increase its visibility.

The term "glandular secretion" means any substance produced by the eccrine, apocrine or sebaceous glands in the friction ridges.

The term "carrier" means a solid substance upon which an indicator is immobilized in a fingermark lifting and visualization device.

The term "reference fingermark" means a fingermark formed by slightly pressing a fingertip onto a clean glass slide. The fingertip may touch the hair or skin, such as the nose, face or scalp, prior to pressing onto the clean glass slide to produce a groomed reference fingermark. Alternatively, the fingermark may be a natural (not groomed) reference fingermark. (Please see International Fingerprint Research Group, "Guidelines for the assessment of fingermark detection techniques", Journal of Forensic Identification, Vol. 64, No. 2, pp. 174-200 (2014) for more information regarding the use of groomed and natural fingermarks.)

A fingermark lifting and visualization device is considered to pass the "fingermark point test" if it is capable of visualizing at least 12 points in a reference fingermark.

A fingermark lifting and visualization device is considered to pass the "basic visualization test" if it is capable of developing a fingermark with at least a Centre for Applied Science & Technology (CAST) Grade 2 and a University of Lausanne (UNIL) assessment of ± after contacting a reference fingermark.

A fingermark lifting and visualization device is considered to pass the "enhanced visualization test" if it is capable of developing a fingermark with at least a Centre for Applied Science & Technology (CAST) Grade 3 and a University of Lausanne (UNIL) assessment of + after contacting a reference fingermark.

A fingermark lifting and visualization device is considered to pass the "basic contact time test" if it is capable of visualizing a fingermark that satisfies the basic visualization test after contacting a reference fingermark for at most 2 minutes.

A fingermark lifting and visualization device is considered to pass the "enhanced contact time test" if it is capable of visualizing a fingermark that satisfies the basic visualization test after contacting a reference fingermark for at most 10 seconds.

A fingermark lifting and visualization device is considered to pass the "basic stability test" if it is capable of visualizing a fingermark that is stable for at least 2 minutes after contacting a reference fingermark.

A fingermark lifting and visualization device is considered to pass the "enhanced stability test" if it is capable of visualizing a fingermark that is stable for at least 2 days after contacting a reference fingermark.

A fingermark lifting and visualization device is considered to pass the "aged fingermark test" if it is capable of visualizing a reference fingermark that is at least four weeks old.

The term "visual spectrum" means electromagnetic radiation having a wavelength of about 390-700 nm that may be observed by the human eye.

All percentages (%) are weight/weight percentages, unless stated otherwise.

All solutions are aqueous, unless stated otherwise.

BRIEF DESCRIPTION OF THE DRAWINGS

The invention can be better understood with reference to the following drawings and description.

DETAILED DESCRIPTION

Figure 1:
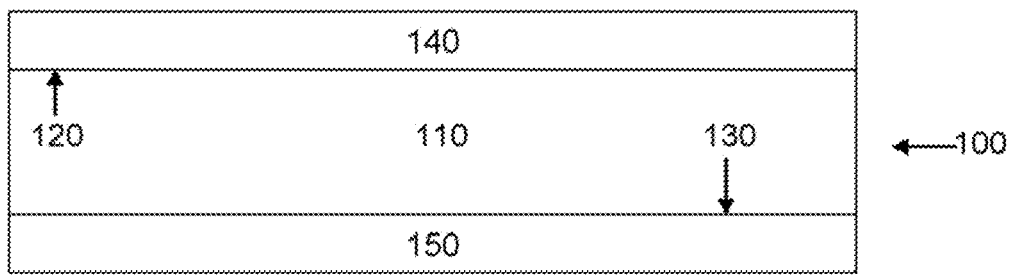
FIG. 1 illustrates a fingermark lifting and visualization device.

Current fingermark lifting devices, such as lifting tapes and gel lifters, suffer from a number of limitations. These devices are known to have limited sensitivity and selectivity for glandular secretions. Older fingermarks are particularly difficult to successfully lift from a substrate. Existing devices also are often unable to detect and lift fingermarks from certain substrates, especially substrates that are highly reflective, patterned, luminescent, reactive, textured and/or porous. In addition, security features included in items such as banknotes, passports and government-issued identification cards to prevent counterfeiting may be visible at wavelengths of light that interfere with common fingermark detection techniques.

Current fingermark lifting devices are particularly unsuitable for detecting fingermarks in covert operations. In these situations, law enforcement officers must be able to gather forensic evidence without leaving visual clues that could be noticed by the subject under surveillance. Removing objects from an area under surveillance for laboratory testing is often not possible, so fingermarks must be detected on site. The use of fingermark developers that leave a visible trace, such as a color change or stain, is unacceptable. Developer powders are also disfavored because there is a significant risk of leaving visible residue after development. The requirements for secrecy make detection of invisible fingermarks extremely challenging or even impossible.

A commercially available device that offers an improvement on traditional lifting devices is the fluorescent blood lifting device available from ZAR-PRO™ (Livonia, Mich.). The ZAR-PRO™ device is a lifter that is capable of detecting bloody and proteinaceous impression evidence ("What is Zar-Pro?", available online at www.zar-pro.com, 2010). While this device may be useful for detecting fingermarks in blood, it is unable to detect invisible fingermarks on a substrate.

The present invention includes a fingermark lifting and visualization device that is capable of detecting invisible fingermarks without the use of developers. The fingermark lifting and visualization device includes a carrier having a lifting surface and an indicator immobilized on the lifting surface. The indicator undergoes a visible color change or a change in fluorescence when it contacts a glandular secretion. The color change or change in fluorescence results from a chemical reaction between the indicator and the glandular secretions, which typically have a pH of about 4-7.

The fingermark lifting and visualization device provides a number of practical advantages over existing devices. Immobilizing the indicator on the carrier allows a single device to both lift and visualize an invisible fingermark. Eliminating the need for a developer allows the device to detect fingermarks on site without leaving any noticeable residue. Producing a visible fingermark without the use of developers or separate fingermark lifters also greatly simplifies the evidence gathering process. These features make the fingermark lifting and visualization device particularly well-suited for detecting fingermarks in covert operations.

The fingermark lifting and visualization device also offers excellent performance. The device is capable of detecting fingermarks on a variety of substrates, including highly reflective, patterned, luminescent, reactive, textured and porous substrates. The device meets the minimum performance criteria of being capable of visualizing at least 12 points in a fingermark, being capable of developing a fingermark with at least a CAST Grade 2 and being capable of developing a fingermark with at least a UNIL assessment of ±. In addition, the device can visualize a fingermark after contacting the fingermark for at most 2 minutes, and produces visualized fingermarks that remain stable for at least 2 minutes. Preferably, the device is capable of detecting older fingermarks, including fingermarks over 4 weeks old. These characteristics demonstrate that the fingermark lifting and visualization device is suitable for field use.

FIG. 1 illustrates a fingermark lifting and visualization device 100. The device includes a carrier 110 having a lifting surface 120 and a support surface 130, opposite the lifting surface. An indicator 140 is immobilized on the lifting surface. An optional backing member 150 is coupled to the support surface.

The carrier may be composed of a polymer. The polymer is preferably flexible and durable. Examples of suitable polymers include nylon, amphoteric nylon, positively charged nylon, negatively charged nylon, polyvinylidene fluoride (PVDF) and polyethylene terephthalate (PET). Preferred polymers include positively charged nylon and polyvinylidene fluoride (PVDF).

The carrier may be provided in any size or shape that is appropriate for lifting and visualizing a fingermark. The length and width of the carrier may each independently have a dimension between 2-100 cm, including 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 35 cm, 40 cm, 45 cm, 50 cm, 55 cm, 60 cm, 65 cm, 70 cm, 75 cm, 80 cm, 85 cm, 90 cm and 95 cm. For example, the carrier may be 2 cm by 2 cm for lifting a single fingermark, or may be 30 cm by 30 cm for lifting multiple fingermarks or a combination of fingermarks and a palm print.

The indicator may be any substance, or a combination of multiple substances, that changes color or changes in fluorescence in the visible spectrum in response to contact with a glandular secretion. The indicator may additionally or alternatively change color in the visible spectrum as a response to radiation in the ultraviolet spectrum (about 10-400 nm) or in the infrared spectrum (about 700 nm-1 mm). The indicator may change color due to a change in its protonation state or undergoing a chemical reaction after interacting with the glandular secretions, which typically have a pH of about 4-7. The indicator may have a pH that is less than 4, including a pH of less than 1, 1, 2 or 3, or may have a pH of greater than 7, including a pH of 8, 9, 10, 11, 12, 13, 14 or greater than 14. The indicator may also be chemically treated to adjust its pH to be less than 4 or greater than 7.

Preferred indicators include pH-sensitive substances and amine-reactive substances. Examples of pH-sensitive substances include phthalides, triarylmethanes, fluorans, azo-dyes, styryl-dyes, and indophenols. Preferred pH-sensitive substances include bromophenol red, phenol red, bromocresol purple, Congo red, methyl red, natural red, bromoxylenol blue, bromothymol blue and bromocresol green. Examples of amine-reactive substances include ninhydrin and ninhydrin derivatives, amido black (sodium 4-amino-5-hydroxy-3-(E)-(4-nitrophenyl)diazenyl)-6-((E)-phenyldiazenyl) naphthalene-2,7-disulfonate), 1,8-diazafluoren-9-one (DFO), 1,2-indanedione, p-dimethylaminocinnamaldehyde (pDMAC), 4-chloro-7-nitrobenzofurazan (NBD chloride), dansyl chloride, o-phthalaldehyde (OPA), fluorescamine (4'-phenylspiro[2-benzofuran-3,2'-furan]-1,3'-dione), genipin (methyl (1R,2R,6S)-2-hydroxy-9-(hydroxymethyl)-3-oxabicyclo[4.3.0]nona-4,8-diene-5-carboxylate), and lawsone (2-hydroxy-1,4-naphthoquinone). A preferred amine-reactive substance is fluorescamine. Particularly preferred indicators include phenol red, bromocresol purple, and fluorescamine.

Alternatively, the indicator may be a pH-sensitive substance that becomes fluorescent in the visible spectrum in response to contact with a glandular secretion. Examples of pH-sensitive substances that become fluorescent after contacting glandular secretions include boron-dipyrromethene (BODIPY) and BODIPY derivatives such as Green DND-26, 1,3,5,7-tetramethyl-8-(4-dimethyl-amino)-4-difluoro-boroa-3a,4a-diaza-(s)-indacene, N,N-dimethylaminophenyl-2,6-dicarboxyethyl-1,3,5,7-tetramethylboron-dipyrromethene (DiMeNBDP), $H_2$NBDP, EtMeNBDP, DiEtNBDP and PhBDP. A preferred pH-sensitive substance that becomes fluorescent after contacting glandular secretions is DiMeNBDP.

The indicator may also be a polymer doped with a pH-sensitive substance or amine-reactive substance. The polymer may be a natural polymer or a synthetic polymer. Examples of suitable natural polymers include gelatin, agarose and dextran. Examples of suitable synthetic polymers include polyacrylates and silicones. A preferred polymer is agarose. The pH-sensitive substance or amine-reactive substance may be incorporated by inclusion during the polymerization process, by co-polymerization or may be covalently bound to a monomer prior to polymerization.

The indicator may be immobilized on the carrier by any suitable process for applying a pH-sensitive substance or an amine-reactive substance to a surface. Preferably, the indicator does not diffuse or bleed after immobilization. Examples of suitable immobilization processes include physical adsorption, covalent immobilization, inclusion, dip coating or spin coating. Alternatively, the indicator may be incorporated in a gel or coating by inclusion or co-polymerization, and the indicator-gel or indicator-coating may then be immobilized on the carrier.

The fingermark lifting and visualization device may optionally include a backing member coupled to the support surface of the carrier. The optional backing member may make the device easier to manipulate when lifting a fingermark. The optional backing member may also help prevent users from inadvertently inducing a color change in the indicator when applying pressure to the device while lifting a fingermark. Preferably the optional backing member is flexible to allow the device to lift fingermarks from curved or irregularly-shaped substrates. Examples of suitable materials for the backing member include elastomers and silicones (polysiloxanes). The backing member may have the same dimensions as the carrier, or may be larger than the carrier.

Figure 2:
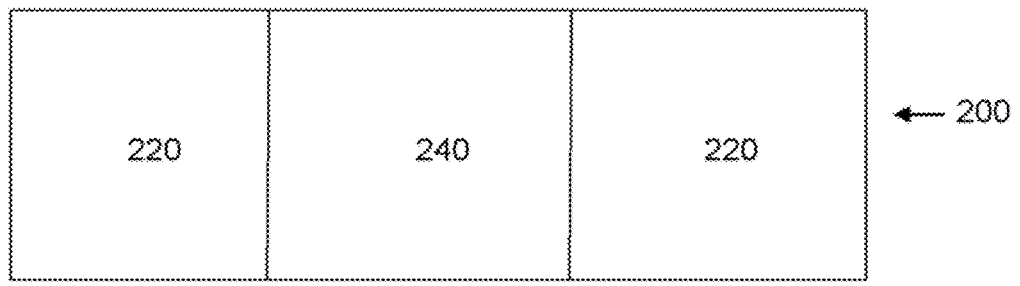
FIG. 2 illustrates a top view of a fingermark lifting and visualization device having a lifting surface and an indicator immobilized on a portion of the lifting surface

The indicator may be immobilized on the entire lifting surface of the carrier (as shown in FIG. 1), or may be immobilized on a portion of the lifting surface of the carrier. FIG. 2 illustrates a top view of a fingermark lifting and visualization device 200 having a lifting surface 220 and an indicator 240 immobilized on a portion of the lifting surface. Areas of the lifting surface where the indicator has not been immobilized on the lifting surface will not react with fingermarks. The non-reactive areas may enhance the practical utility of the device, such as by providing areas for handling the device, taking notes or adding a measurement scale. The non-reactive areas may also be marked with a unique identifier, such as a serial number or quick response (QR) code.

Figure 3:
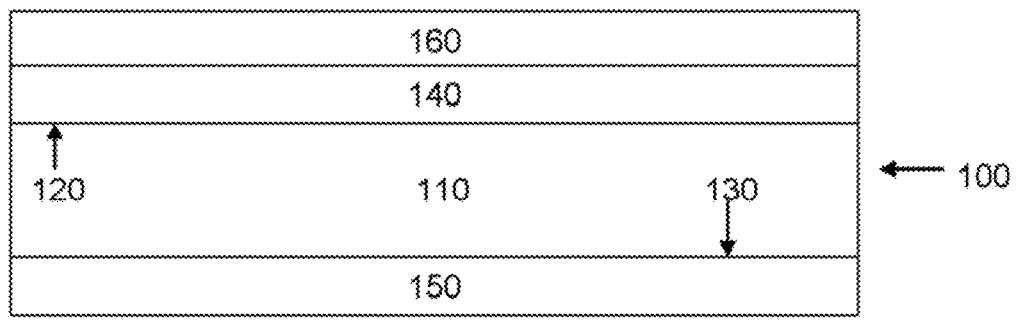
FIG. 3 illustrates a fingermark lifting and visualization device with an optional cover.

FIG. 3 illustrates the fingermark lifting and visualization device 100 shown in FIG. 1 with an optional cover 160 on the indicator 140. The cover protects the indicator when not in use by preventing the indicator from contamination or unintentional contact with a fingermark. The cover is preferably a flexible, clear substance, such as a polymer. The cover may be designed to be removed and discarded. Alternatively, the cover may be designed to be reapplied to the device to protect the indicator after it has contacted a fingermark. For example, the cover may be coupled to the device, such as by a flexible hinge, or may include an adhesive to allow the cover to be affixed to the device.

The performance of the fingermark lifting and visualization device may be evaluated by subjecting it to one or more tests involving the lifting and visualization of a reference fingermark. The device may be evaluated based on the amount of detail shown in a visualized fingermark. A device that is capable of visualizing at least 12 points in a reference fingermark passes the "fingermark point test". Passing the fingermark point test is necessary for a fingermark lifting and visualization device to be considered safe for identification purposes. Preferably, the device of the present invention passes the fingermark point test. An example of a lifted and visualized fingermark with at least 12 distinct points identified may be seen in FIG. 19.

The device may be evaluated under the CAST and/or UNIL fingermark grading schemes. A fingermark lifting and visualization device is considered to pass the "basic visualization test" if it is capable of developing a fingermark with at least a CAST Grade 2 and a UNIL assessment of ± after contacting a reference fingermark. A fingermark lifting and visualization device is considered to pass the "enhanced visualization test" if it is capable of developing a fingermark with at least a CAST Grade 3 and a UNIL assessment of + after contacting a reference fingermark. Preferably, the device of the present invention passes the basic visualization test. More preferably, the device of the present invention passes the enhanced visualization test.

The device may be evaluated based on the time required to contact a fingermark for visualization. A fingermark lifting and visualization device that is capable of visualizing a fingermark that satisfies the basic visualization test after contacting a reference fingermark for at most 2 minutes is considered to pass the "basic contact time test". A fingermark lifting and visualization device that is capable of visualizing a fingermark that satisfies the enhanced visualization test after contacting a reference fingermark for at most 10 seconds is considered to pass the "enhanced contact time test". Preferably, the device of the present invention passes the basic contact time test. More preferably, the device of the present invention passes the enhanced contact time test.

The device may be evaluated based on the duration of time that a visualized fingermark remains visible on the device. A fingermark lifting and visualization device that is capable of visualizing a fingermark for at least 2 minutes after contacting a reference fingermark is considered to pass the "basic stability test". A fingermark lifting and visualization device that is capable of visualizing a fingermark for at least 2 days after contacting a reference fingermark is considered to pass the "enhanced stability test". A visualized fingermark that has faded or become difficult to see on the device may be enhanced by exposing the fingermark to ultraviolet (UV) light in a dark room. Preferably, the UV light has a wavelength of 280-390 nm. Preferably, the device of the present invention passes the basic stability test. More preferably, the device of the present invention passes the enhanced stability test.

The device may be evaluated based on its capability to lift and visualize a fingermark that has been deposited on a substrate for an extended period of time prior to detection. A fingermark lifting and visualization device that is capable of lifting and visualizing a reference fingermark that is at least four weeks old is considered to pass the "aged fingermark test". Preferably, the device of the present invention passes the aged fingermark test.

Figure 4:
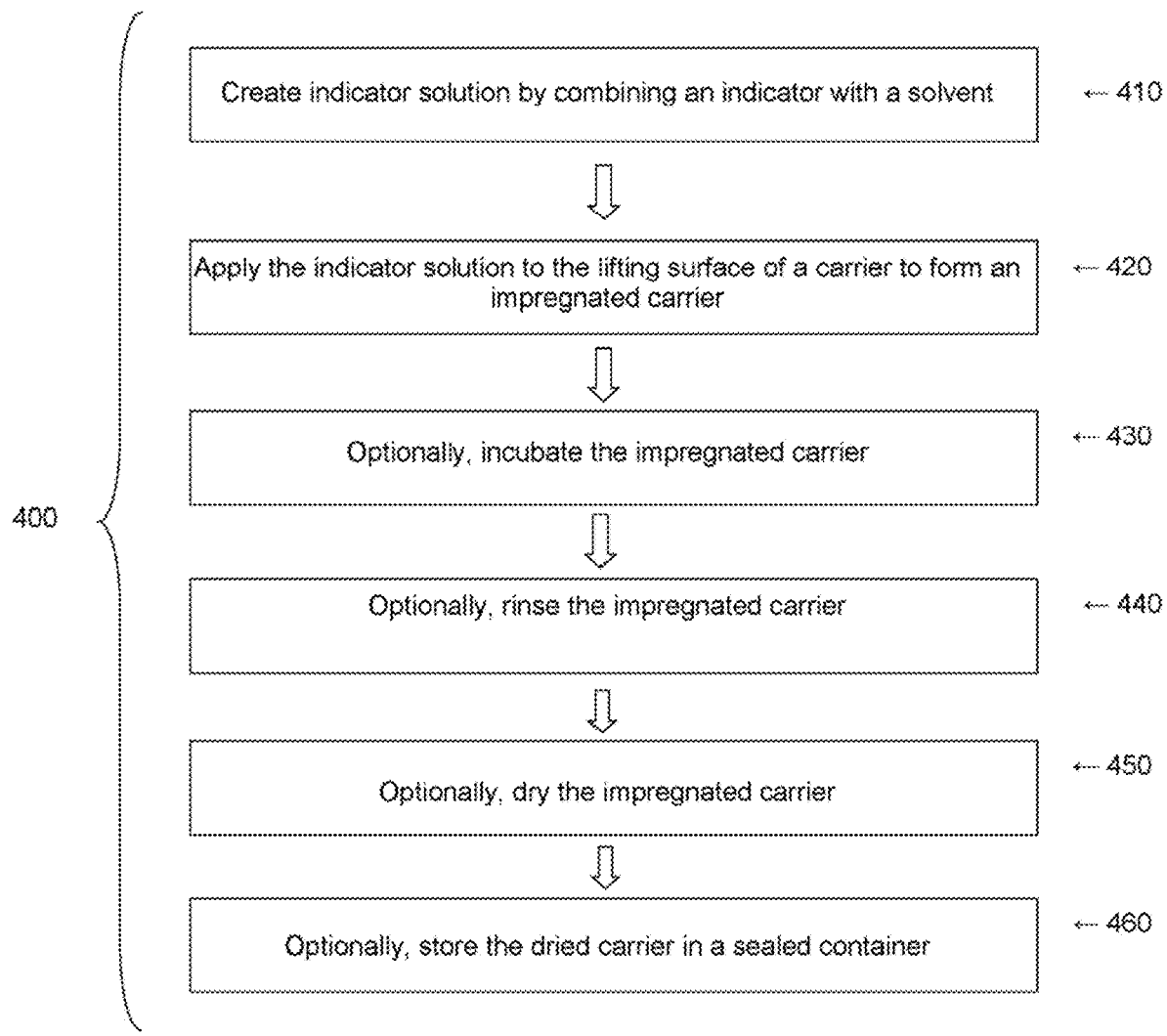
FIG. 4 illustrates a method of making a fingermark lifting and visualization device.

FIG. 4 illustrates a method of making a fingermark lifting and visualization device at 400. First, an indicator solution is created by combining an indicator with a solvent at 410. Next, the indicator solution is applied to the lifting surface of a carrier to form an impregnated carrier at 420. Then, optionally, the impregnated carrier may be incubated at 430. The impregnated carrier may optionally be rinsed after incubation at 440. Finally, optionally, the impregnated carrier may be dried at 450. The dried impregnated carrier may optionally be stored in a sealed container at 460.

The indicator solution may be formed by selecting a solvent that is suitable for the indicator being used. The solvent may be used to adjust the pH of the indicator to be below 4 or greater than 7 to ensure a reaction with glandular secretions. 50% ethanol in NaOH is a preferred solvent for pH-sensitive indicators while 75% ethanol in water is a preferred solvent for amine-reactive indicators. For indicator-doped pH-sensitive polymers, a preferred solvent is 0.0006-0.003 M NaOH. The optimal concentration will depend on the specific indicator being used. For example, phenol red-doped agarose may be mixed with 0.002-0.003 M NaOH while bromocresol purple-doped agarose may be mixed with 0.0006-0.0008 M NaOH. Preferably, the polymer is present in an amount of 1% w/v. Indicator-doped pH-sensitive polymers are preferably heated to boiling after mixing.

The indicator solution may be applied to the carrier by placing the carrier in a vessel, such as a petri dish, and adding a sufficient amount of indicator solution to submerge the carrier. The concentration of the indicator solution may be varied to achieve a desired color of indicator on the carrier. For example, the concentration of a phenol red indicator solution may be varied to produce a pink, salmon or red colored indicator.

The impregnated carrier may optionally be incubated under conditions that are appropriate for the specific indicator. Preferably the impregnated carrier is incubated for 2-24 hours at room temperature (18-21° C.). The incubation conditions may be varied to achieve a desired color of indicator. The impregnated carrier may optionally be placed on a rotator. The impregnated carrier may optionally be protected from light during the incubation.

The impregnated carrier may optionally be rinsed after incubation. Rinsing the impregnated carrier with a reagent that adjusts the pH of the indicator to be below 4 or greater than 7 ensures that the indicator will react with glandular secretions with sufficient contrast. For example, an impregnated carrier may be rinsed with sodium hydroxide to raise its pH to above 7, or may be rinsed with hydrochloric acid to lower its pH to below 4. The specific rinsing reagent may be selected based on the indicator used.

The impregnated carrier may optionally be dried for 3-60 minutes after incubation in open air or in an inert atmosphere. The drying conditions may be varied based on the immobilization and rinsing conditions.

The fingermark lifting and visualization device may optionally be stored in a sealed container before use. Preferably the container is vacuum-sealed. Special sealing precautions may be necessary depending on the type of indicator being used. For example, pH-sensitive indicators that have been adjusted to have a pH greater than 7 must be stored in a container that does not include a coating with acidic groups. Similarly, amine-reactive indicators must be stored in a container that does not include a coating with amines. The sealed container may contain substances that control the moisture level within the sealed container, such as propylene glycol or appropriate humidifying polymers. Preferably, the devices are protected from light when stored.

Figure 5:
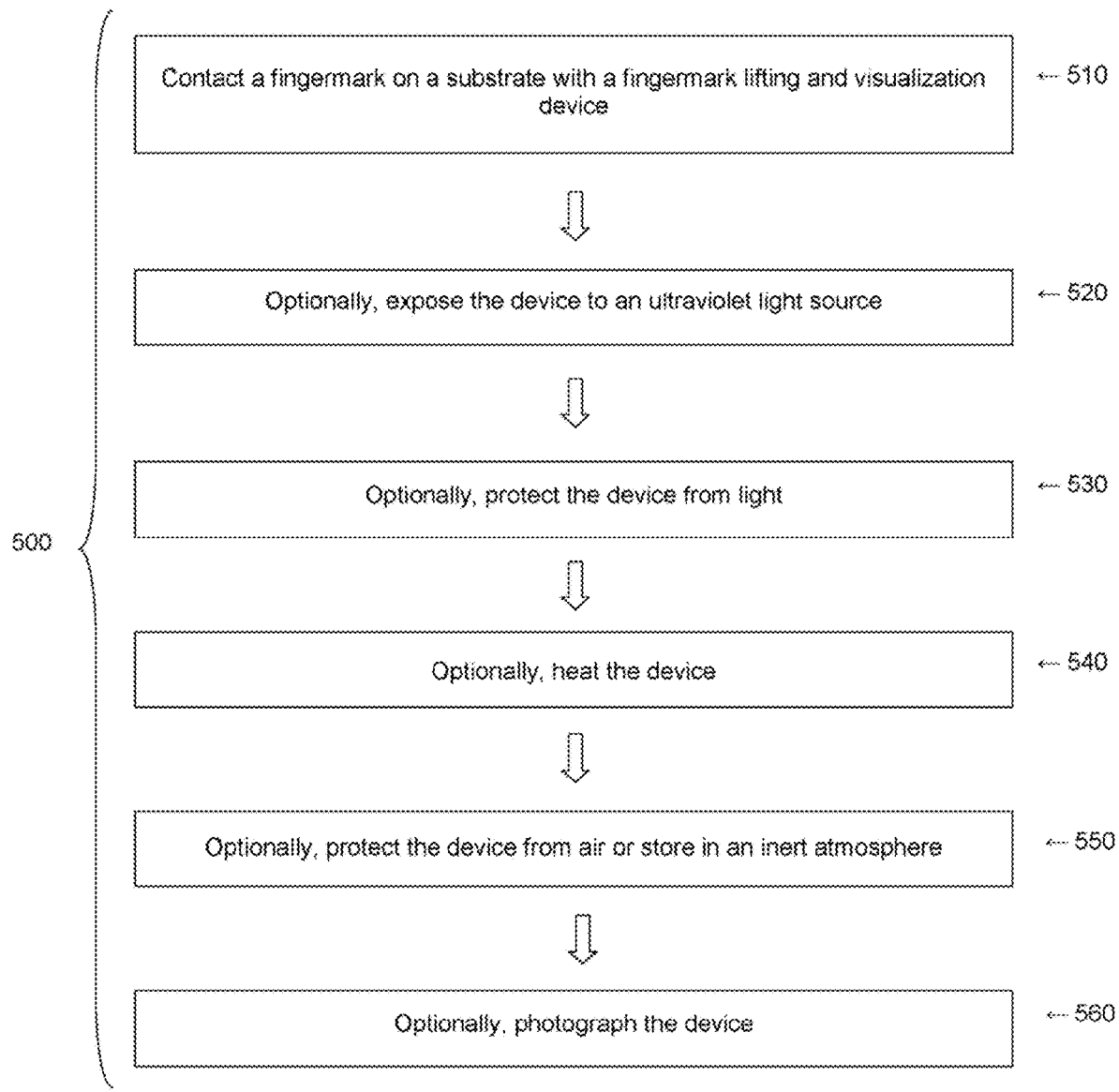
FIG. 5 illustrates a method of visualizing a fingermark on a substrate.

FIG. 5 illustrates a method of visualizing a fingermark on a substrate at 500. First, a fingermark lifting and visualization device contacts the fingermark on the substrate to cause an image of the fingermark to form on the device at 510. Optionally, the device may be exposed to an ultraviolet light source after contacting the fingermark to allow a fluorescent indicator to emit light at 520. Optionally, the device may be protected from light after contacting the fingermark at 530. Optionally, the device may be heated at 540. Optionally, the device may be protected from air or stored in an inert atmosphere (for example, nitrogen or argon) at 550. Optionally, the device may be photographed after contacting and visualizing the fingermark at 560. If performed, optional steps 520, 530, 540, 550 and 560 may be performed in any order. No additional development steps such as powdering or cyanoacrylate fuming are required to detect and visualize the fingermark.

The substrate may be any substrate that is capable of bearing a fingermark. Preferred substrates for obtaining fingermarks are glass, plastic and metals. The substrate may include features or surface treatments such as being highly reflective, patterned, luminescent, reactive, textured and/or porous.

The fingermark lifting and visualization device may contact the fingermark for a sufficient amount of time for the indicator to react with the glandular secretions on the substrate and undergo a visible color change or other change allowing for visualization. Suitable contact times range from 5 seconds-2 minutes. Preferably, the device contacts the fingermark for 5-10 seconds.

The fingermark lifting and visualization device may optionally be exposed to an ultraviolet light source after contacting the fingermark. Certain fluorescent indicators may absorb ultraviolet light and emit light. The emission preferably occurs in the visible spectrum and does not require a specialized camera for detection. Examples of ultraviolet light sources include ultraviolet lamps and ultraviolet flashlights.

The fingermark lifting and visualization device may optionally be protected from visible light after contacting the fingermark. Although not required for visualization, the image of the fingermark formed on the device may be enhanced if the device is protected from light after contacting the fingermark. Protection from visible light may be beneficial for devices that include amine-reactive indicators.

The fingermark lifting and visualization device may optionally be heated after contacting the fingermark. Any heat source that is capable of warming the carrier and indicator without destroying either component may be used. Example of suitable heat sources include hot plates and heat presses.

The fingermark lifting and visualization device may optionally be protected from air or stored in an inert atmosphere after contacting the fingermark. Any suitable process for protecting a substance from air may be used. An example of a process for protecting the device from air is vacuum sealing. Examples of inert atmosphere include non-reactive gases such as nitrogen or argon.

The fingermark lifting and visualization device may optionally be photographed after contacting the fingermark. Any type of camera may be used to photograph the device. Examples of suitable cameras include film cameras, single-lens reflex (SLR) cameras, digital cameras, digital single-lens reflex (DSLR) cameras and cameras included in portable devices such as cellular phones and tablets. A preferred camera is a digital single lens reflex (DSLR) camera. The device may be photographed under ambient light or under an ultraviolet light source.

EXAMPLES

Example 1

General Procedure for Preparing a Fingermark Lifting and Visualization Device including a Phenol Red-Doped Agarose Indicator A fingermark lifting and visualization device including a pH-sensitive indicator was prepared. A 0.2-0.3 mg/mL solution of phenol red was mixed with 1% w/v of agarose in a flask containing 0.002-0.003 M NaOH. The flask was plugged with KIMWIPES® and microwaved until boiling, about 30 seconds at 900 W. The flask was then swirled. 5-8 mL of the boiled solution was poured into a 100 mm×15 mm plastic dish. A positively charged nylon (ROCHE®) carrier was then placed in the dish. The dish was covered and the carrier allowed to incubate at room temperature (18-21° C.) overnight. The incubated carrier was then removed from the dish, placed on a KIMWIPE® with the surface that contacted the phenol red-agarose solution facing up and allowed to dry in open air for 30-60 minutes.

Example 2

General Procedure for Lifting and Visualizing a Fingermark with a Fingermark Lifting and Visualization Device including a Phenol Red-Doped Agarose Indicator A fingermark lifting and visualization device was prepared as described in Example 1. The lifting surface of the device was pressed on a substrate bearing an invisible fingermark for 5-10 seconds. The fingermark was visualized on the device. The fingermark remained visible for 2-4 days with the device left in open air.

Example 3

General Procedure for Preparing a Fingermark Lifting and Visualization Device including a Phenol Red Indicator A fingermark lifting and visualization device including a pH-sensitive indicator was prepared. A 0.2-0.3 mg/mL solution of phenol red was mixed with a 50% ethanol/50% 0.004 M NaOH solution. A positively charged nylon (ROCHE®) carrier was then placed in a dish. Enough solution was poured in the dish to fully submerge the carrier. The dish was then placed on a rotator for 2 hours at room temperature (18-21° C.). The incubated carrier was removed and washed by spraying 95% ethanol on both sides until the color was uniform. The surface was then dabbed lightly with a KIMWIPE® to remove any droplets or pools of solution. The incubated carrier was then allowed to dry for 8-14 minutes in open air.

Example 4

General Procedure for Lifting and Visualizing a Fingermark with a Fingermark Lifting and Visualization Device including a Phenol Red Indicator A fingermark lifting and visualization device was prepared as described in Example 3. The lifting surface of the device was pressed on a substrate bearing an invisible fingermark for 5 seconds. The fingermark was visualized on the device. The fingermark remained visible for 7-10 days with the device left in open air.

Example 5

General Procedure for Preparing a Fingermark Lifting and Visualization Device including a Fluorescamine Indicator A fingermark lifting and visualization device including an amine-reactive indicator was prepared. 0.25 mg/mL of fluorescamine was added to a solution of 75% ethanol in water. A PVDF carrier was placed in a dish. Enough solution was poured in the dish to fully submerge the carrier. The dish was then placed on a rotator for 2 hours at room temperature (18-21° C.) and protected from light. The incubated carrier was then removed from the dish and placed on a KIMWIPE®. The surface was then dabbed lightly with a KIMWIPE® to remove any droplets or pools of solution. The incubated carrier was then allowed to dry for 3-30 minutes in open air.

Example 6

General Procedure for Lifting and Visualizing a Fingermark with a Fingermark Lifting and Visualization Device including a Fluorescamine Indicator A fingermark lifting and visualization device was prepared as described in Example 5. The lifting surface of the device was pressed on a substrate bearing an invisible fingermark for 10 seconds. The fingermark was visualized on the device. The fingermark remained visible for several days with the device left in open air.

Example 7

Figure 6:
FIG. 6 is a photograph of a fingermark that was deposited and visualized on a fingermark lifting and visualization device with a bromocresol purple indicator.

Fingermark Detection and Visualization with Fingermark Lifting and Visualization Devices including Phenol Red and Bromocresol Purple Indicators Phenol red and bromocresol purple indicators were each immobilized onto positively charged nylon carriers to form fingermark lifting and visualization devices. The impregnated carriers were then rinsed briefly with a basic solution. A finger was then pressed onto the devices to directly deposit a fingermark. The device with the phenol red indicator displayed a yellowish friction ridge pattern on a fuchsia background, but quickly faded. The device with the bromocresol purple indicator displayed a yellowish friction ridge pattern on a purple background for several minutes. The fingermark was visible long enough to permit the taking of photographs with a standard NIKON® DSLR camera under ambient light. FIG. 6 is a photograph of the fingermark that was visualized on the device with the bromocresol purple indicator.

A second set of fingermark lifting and visualization devices was prepared in the same manner. A finger was then pressed onto the devices to directly deposit a fingermark. The devices were then stored under nitrogen. The visualized fingermarks remained visible on both devices after three days. These results indicate that the stability of a visualized fingermark may be increased by storing the device in an inert atmosphere.

A third set of fingermark lifting and visualization devices was prepared. As compared to the first set of devices, these devices were dried after rinsing with the basic solution. A finger was then pressed onto the devices to directly deposit a fingermark. The visualized fingermarks remained visible on both devices for over 7 days under open air. These results indicate that the stability of a visualized fingermark may be increased by drying the device prior to detecting a fingermark.

Example 8

Figure 7:
FIG. 7 is a photograph of a fingermark that was lifted from a glass slide and visualized on a fingermark lifting and visualization device with a bromocresol purple indicator.

Fingermark Detection and Visualization with Fingermark Lifting and Visualization Devices including Bromocresol Purple Indicators A fingermark lifting and visualization device with a bromocresol purple indicator immobilized on a nylon carrier was prepared. A finger was applied to a glass slide to deposit a fingermark. The device was then applied to the glass slide for about 5 seconds. The device was able to lift and visualize the fingermark with good ridge detail. The fingermark was visible long enough to permit the taking of photographs with a standard NIKON® DSLR camera under ambient light. FIG. 7 is a photograph of the fingermark that was lifted and visualized.

A second fingermark lifting and visualization device with a bromocresol purple indicator immobilized on a nylon carrier was prepared. The device was then applied to a glass slide upon which a fingermark had been deposited 4 weeks ago. The device was able to lift and visualize the 4-week-old fingermark.

These results demonstrate that the fingermark lifting and visualization devices are capable of lifting and visualizing fresh and aged fingermarks on a substrate. No transfer of color from the carrier to the substrate was observed, which indicates the indicator was sufficiently immobilized on the carrier. In addition, the absence of color transfer confirms the suitability of the devices for covert lifting and visualization of invisible fingermarks.

Example 9

Comparative Test of pH-Sensitive Indicators

Figure 8:
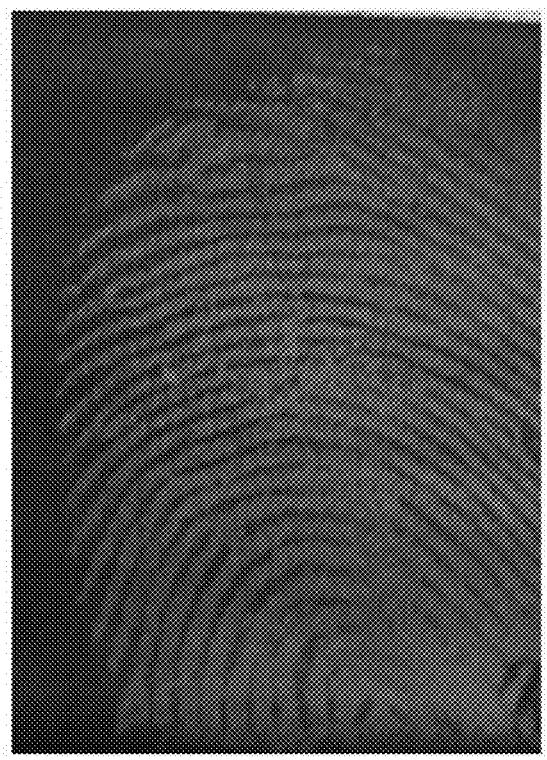
FIG. 8 is a photograph of a fingermark that was deposited and visualized on a fingermark lifting and visualization device with a Congo red indicator.
Figure 9:
FIG. 9 is a photograph of a fingermark that was deposited and visualized on a fingermark lifting and visualization device with a methyl red indicator.
Figure 10:
FIG. 10 is a photograph of a fingermark that was deposited and visualized on a fingermark lifting and visualization device with a bromocresol green indicator.

The performance of Congo red, methyl red and bromocresol green as pH-sensitive indicators was compared. Fingermark lifting and visualization devices were prepared by immobilizing each of the indicators on a separate carrier. A finger was then pressed onto the devices to directly deposit a fingermark. The fingermarks were visible long enough to permit the taking of photographs with a standard NIKON® DSLR camera under ambient light. FIG. 8 is a photograph of the fingermark that was visualized with the Congo red indicator. FIG. 9 is a photograph of the fingermark that was visualized with the methyl red indicator. FIG. 10 is a photograph of the fingermark that was visualized with the bromocresol green indicator. As may be seen in FIGS. 8-10, devices with Congo red or bromocresol green indicators can visualize a fingermark in high contrast with the carrier, while devices with a methyl red indicator can visualize a fingermark with weak contrast with the carrier. These results demonstrate the importance of selecting an appropriate indicator when preparing a fingermark lifting and visualization device.

Example 10

Figure 11:
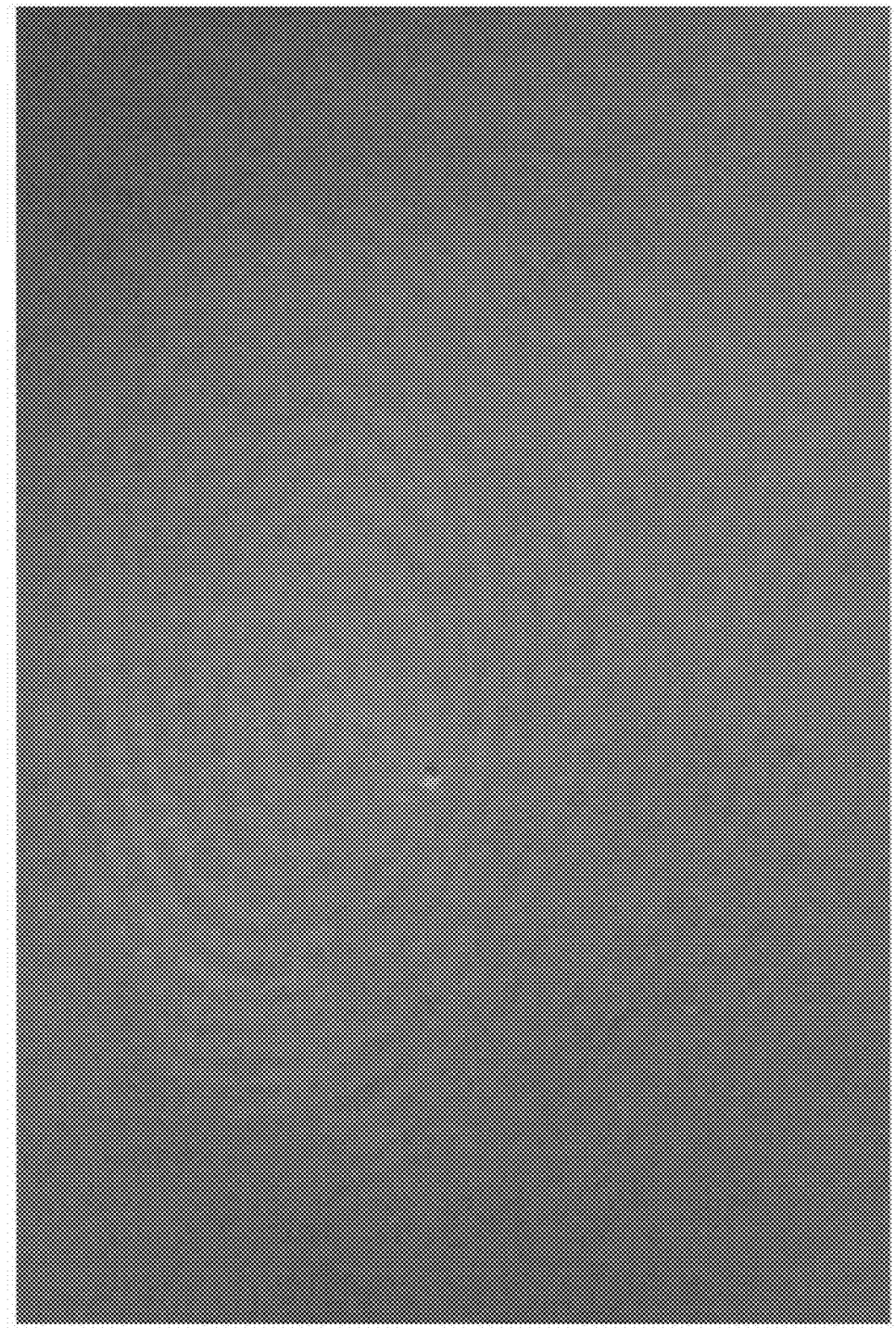
FIG. 11 is a photograph of a fingermark that was lifted from a glass slide and visualized on a fingermark lifting and visualization device containing bromocresol purple-doped agarose.

Fingermark Detection and Visualization with Fingermark Lifting and Visualization Devices including Bromocresol Purple-Doped Agarose Indicators Fingermark lifting and visualization devices with bromocresol purple-doped agarose indicators were prepared. A finger was applied to a glass slide to deposit a fingermark. A device was then applied to the glass slide. The device was able to lift and visualize the fingermark. The fingermark was visible long enough to permit the taking of photographs with a standard NIKON® DSLR camera under ambient light. FIG. 11 is a photograph of the fingermark that was lifted and visualized.

Figure 12:
FIG. 12 is a photograph of a fingermark that was deposited and visualized on a fingermark lifting and visualization device containing bromocresol purple-doped agarose.

A finger was also pressed onto a similar device to directly deposit a fingermark. The fingermark was visible long enough to permit the taking of photographs with a standard NIKON® DSLR camera under ambient light. FIG. 12 is a photograph of the fingermark that was visualized on the device.

These results demonstrate that polymers doped with pH-sensitive substances are appropriate indicators for lifting and visualization of invisible fingermarks.

Example 11

Figure 13:
FIG. 13 is a photograph of a fingermark that was deposited and visualized on a fingermark lifting and visualization device with a ninhydrin indicator.

Fingermark Detection and Visualization with Fingermark Lifting and Visualization Devices including Ninhydrin Indicators Fingermark lifting and visualization devices were prepared by adsorbing ninhydrin on positively charged nylon carriers. A finger was pressed onto a device to directly deposit a fingermark. The device was then heated. The fingermark was visible long enough to permit the taking of photographs with a standard NIKON® DSLR camera under ambient light. FIG. 13 is a photograph of the fingermark that was visualized on the device.

A finger was applied to a glass slide and to a paper to deposit fingermarks. A device was then applied to the glass slide and to the paper. The device was able to lift and visualize the fingermark from the glass slide, however the color formation was weak. No fingermark was lifted and visualized from the paper.

These results demonstrate that amine-reactive substances are appropriate indicators for lifting and visualization of invisible fingermarks. The results also demonstrate how the substrate upon which a fingermark is deposited can impact device performance.

Example 12

Figure 14:
FIG. 14 is a photograph of a fingermark that was deposited and visualized on a fingermark lifting and visualization device with a fluorescamine indicator.

Fingermark Detection and Visualization with Fingermark Lifting and Visualization Devices including Fluorescamine Indicators Fingermark lifting and visualization devices were prepared by adsorbing fluorescamine on PVDF carriers. A finger was pressed onto a device to directly deposit a fingermark. A fingermark was visualized on the device with good ridge detail. The fingermark was visible long enough to permit the taking of photographs with a standard NIKON® DSLR camera under a handheld ultraviolet lamp. FIG. 14 is a photograph of the fingermark that was visualized on the device. The visualized fingermark was stable for over two weeks.

Figure 15:
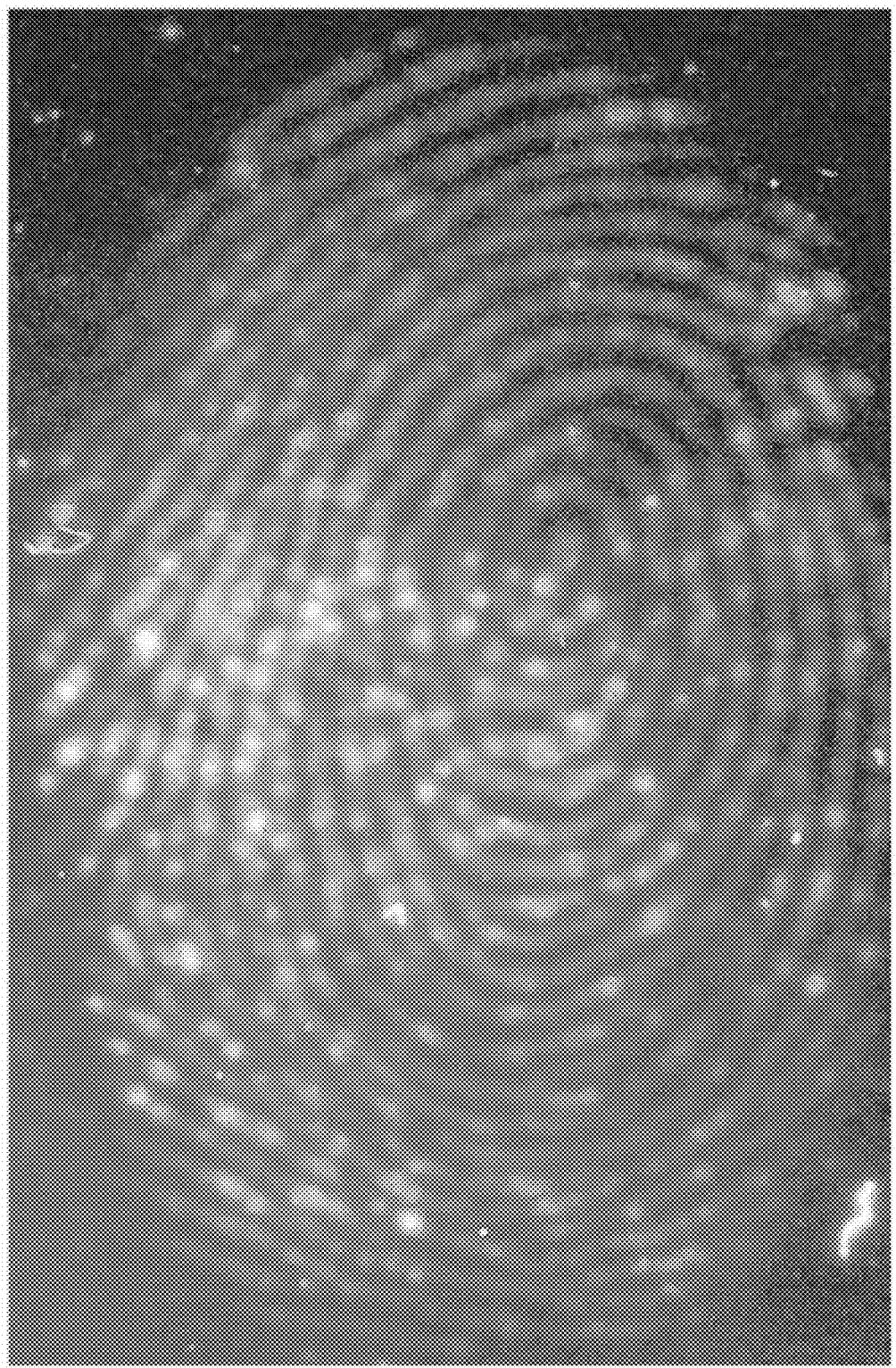
FIG. 15 is a photograph of a fingermark that was lifted from a glass slide and visualized on a fingermark lifting and visualization device with a fluorescamine indicator.
Figure 16:
FIG. 16 is a photograph of a fingermark that was lifted from paper and visualized on a fingermark lifting and visualization device with a fluorescamine indicator.

A finger was applied to a glass slide and to standard printer paper to deposit fingermarks. Devices were then applied to the glass slide and to the paper. The devices were able to lift and visualize the fingermark from the glass slide and from the paper. The fingermarks were visible long enough to permit the taking of photographs. FIG. 15 is a photograph taken with a standard NIKON® DSLR camera under a handheld ultraviolet lamp of the fingermark that was lifted from the glass slide and visualized on the device. FIG. 16 is a photograph taken with a cell phone camera under a handheld ultraviolet lamp of the fingermark that was lifted from the paper and visualized on the device. The visualized fingermarks were stable for over two weeks.

Figure 17:
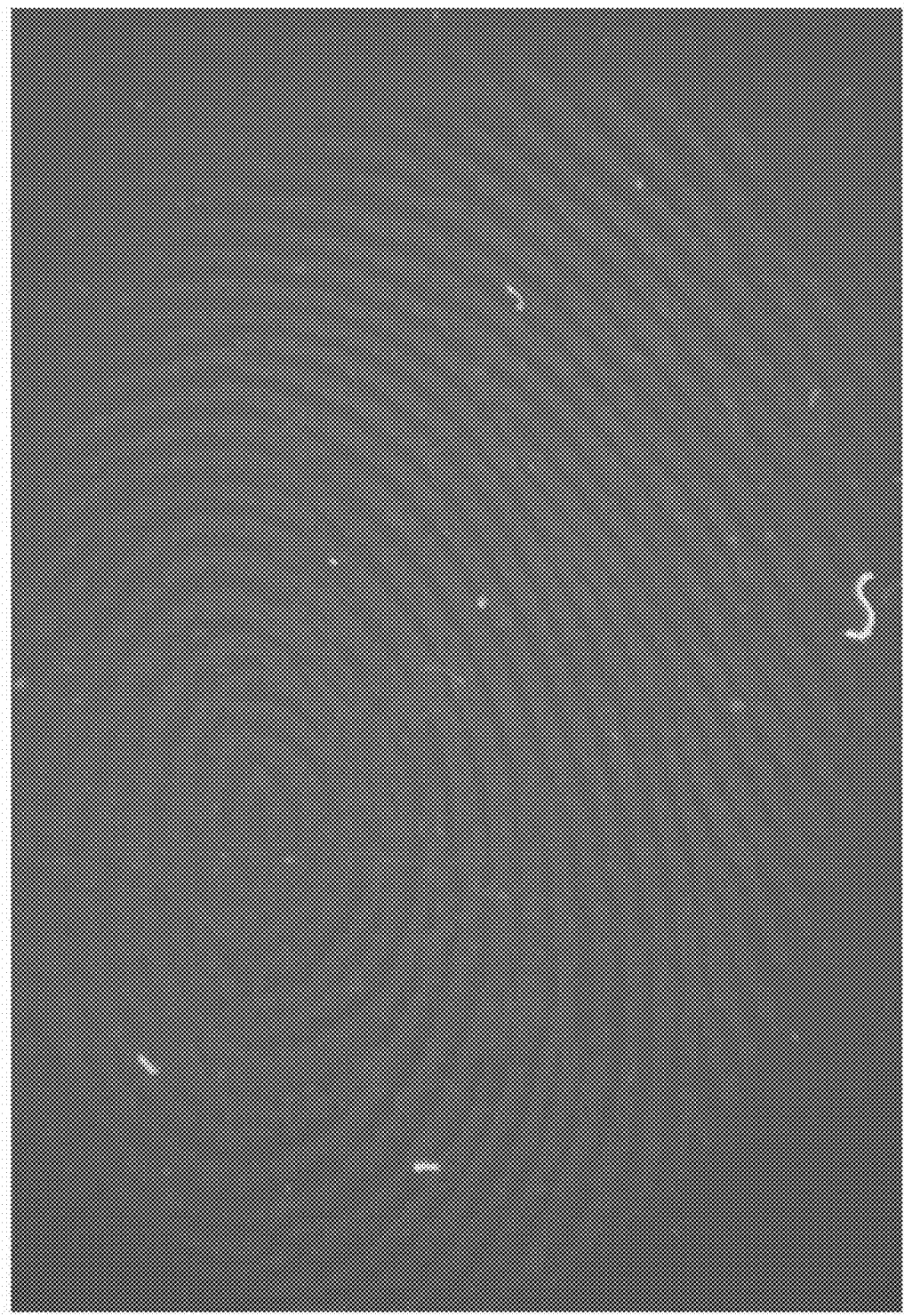
FIG. 17 is a photograph of a fingermark that was deposited and visualized on fluorescamine-doped agarose.

A fluorescamine-doped agarose indicator was prepared and poured into a petri dish. A finger was pressed onto the fluorescamine-doped agarose to directly deposit a fingermark. A fingermark was visualized on the fluorescamine-doped agarose. The fingermark was visible long enough to permit the taking of photographs with a standard NIKON® DSLR camera under a handheld ultraviolet lamp. FIG. 17 is a photograph of the fingermark that was visualized on the fluorescamine-doped agarose. The visualized fingermark was stable for over two weeks.

These results demonstrate that amine-reactive indicators are appropriate indicators for lifting and visualization of fingermarks from a variety of substrates, and that such visualized fingermarks are highly stable. The results also demonstrate the viability of using amine-reactive doped polymers as indicators.

Example 13

Figure 18:
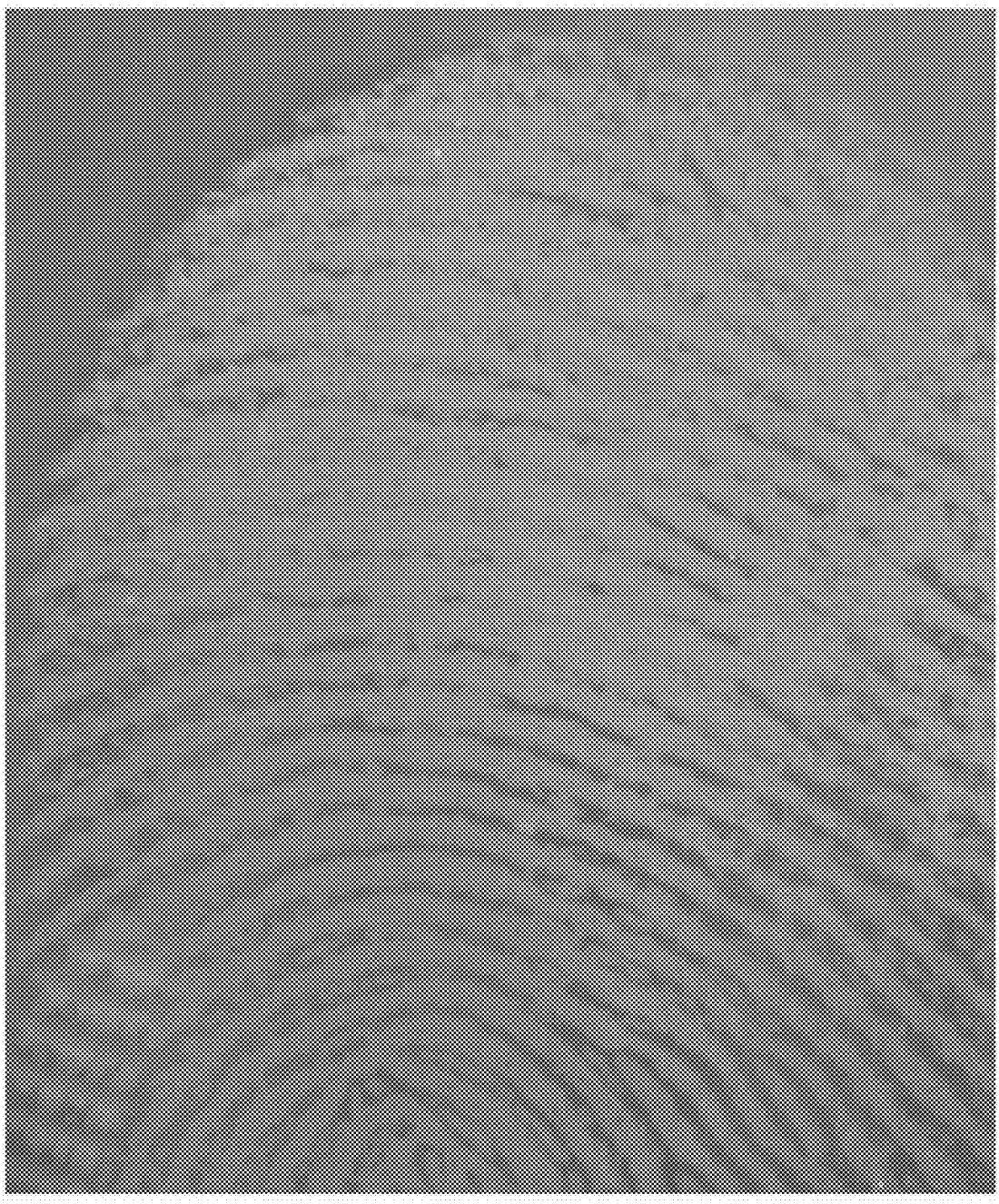
FIG. 18 is a photograph of a fingermark that was deposited and visualized on a fingermark lifting and visualization device with an N,N-dimethylaminophenyl-2,6-dicarboxyethyl-1,3,5,7-tetramethylboron-dipyrromethene (DiMeNBDP) indicator.

Fingermark Detection and Visualization with Fingermark Lifting and Visualization Devices including DiMeNBDP Indicators Fingermark lifting and visualization devices were prepared by immobilizing N,N-dimethylaminophenyl-2,6-dicarboxyethyl-1,3,5,7-tetramethylboron-dipyrromethene (DiMeNBDP) on nylon carriers. A finger was pressed onto a device to directly deposit a fingermark. The fingermark was visualized on the device. The fingermark was visible long enough to permit the taking of photographs with a standard NIKON® DSLR camera under a handheld ultraviolet lamp. FIG. 18 is a photograph of the fingermark that was visualized on the device. The device also was able to lift a fingermark from a substrate.

A fingermark lifting and visualization device with a DiMeNBDP-doped agarose indicator was prepared. The device was able to visualize a fingermark.

These results demonstrate that pH-sensitive fluorescent substances, including polymers doped with pH-sensitive substances, are appropriate indicators for lifting and visualization of fingermarks. The results also demonstrate the viability of using BODIPY-derivatives as indicators.

Example 14

Fingermark Point Test

Figure 19:
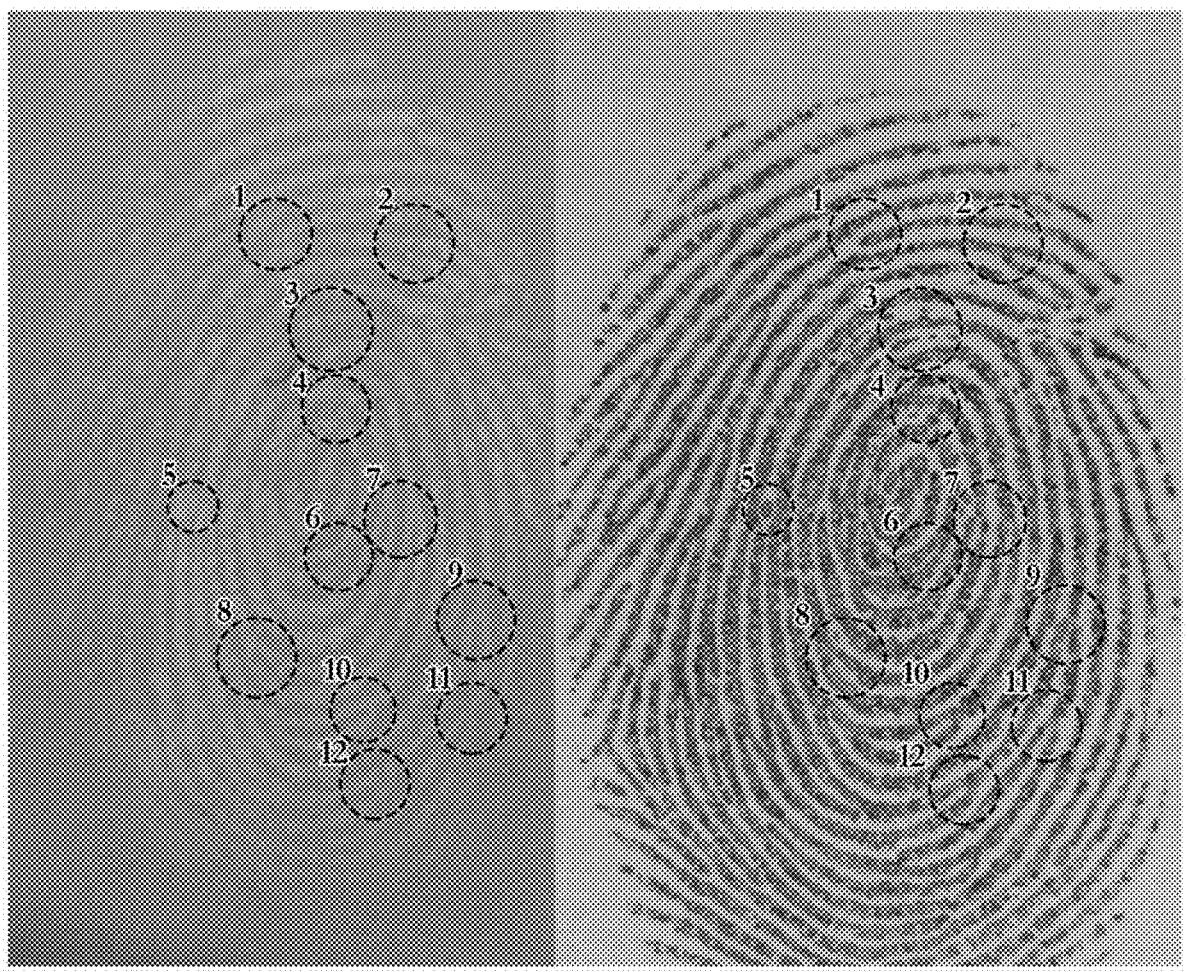
FIG. 19 is a photograph of a fingermark that was lifted from a glass slide and visualized on a fingermark lifting and visualization device with a phenol red indicator with 12 distinct points identified, and a photograph of an exemplar fingermark that was deposited on paper with 12 distinct points identified.

A fingermark lifting and visualization device with a phenol red indicator as described above was prepared. A finger was pressed onto a glass slide to deposit a fingermark. The device was then applied to the glass slide. The device was able to lift and visualize the fingermark. The fingermark was visible long enough to permit the taking of photographs with a NIKON® DSLR camera. The finger was also inked and applied to paper to produce an exemplar fingermark. The exemplar fingermark was photographed with a NIKON® DSLR camera. FIG. 19 is a photograph of the fingermark that was lifted and visualized on the device with 12 distinct points identified, and a photograph of the exemplar fingermark with 12 distinct points identified The photographs shown in FIG. 19 have been annotated to identify 12 distinct points on the visualized fingermark and the exemplar fingermark. The 12 points include (1) a ridge end; (2) a bifurcation; (3) short ridges and dots; (4) a short ridge, dot and bifurcation; (5) a dot; (6) a bifurcation; (7) two bifurcations; (8) a sweat pore, dot and bifurcation; (9) a bifurcation; (10) a bifurcation; (11) a bifurcation; and (12) a bifurcation. The device passed the fingermark point test since it was able to visualize at least 12 points in a reference fingermark.

Example 15

Preparation and Use of a Fingermark Lifting and Visualization Device including a Phenol Red Indicator A fingermark lifting and visualization device with a phenol red indicator was prepared. A solution was prepared by mixing 50% ethanol (95%) and 50% aqueous NaOH (0.004 M). Phenol red was added at a concentration of 0.2 mg/mL to create an indicator solution. A 20-30 $cm^2$ sheet of positively charged nylon carrier was placed in a petri dish and incubated with 10 mL of the indicator solution for 2 hours. The incubated carrier was then removed and washed on both sides with 95% ethanol from a wash bottle, dabbed with a KIMWIPE® to remove moist spots and placed on a clean KIMWIPE® to dry in open air for 12 minutes. The dried incubated carrier was then taped to a slightly bigger sheet of PVDF using SCOTCH® tape along one edge.

Figure 20:
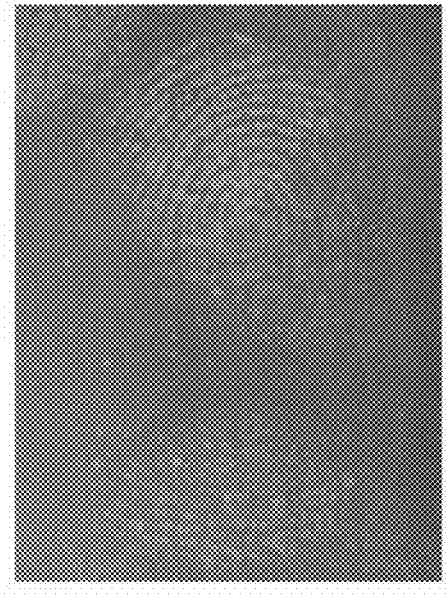
FIG. 20 is a photograph of a fingermark that was lifted from a hardwound brown janitorial paper towel and visualized on a fingermark lifting and visualization device with a phenol red indicator.
Figure 21:
FIG. 21 is a photograph of a fingermark that was lifted from printer paper and visualized on a fingermark lifting and visualization device with a phenol red indicator.
Figure 22:
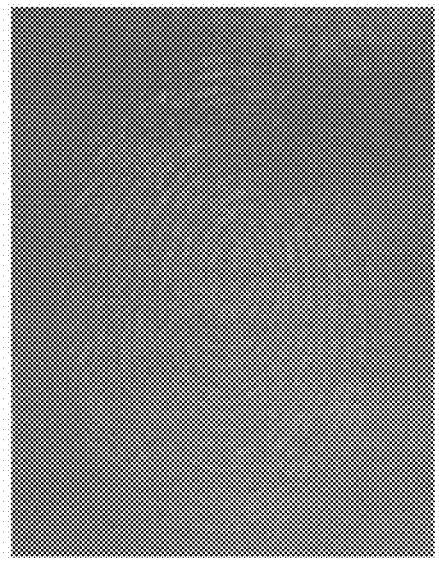
FIG. 22 is a photograph of a fingermark that was lifted from semi-glossy paper and visualized on a fingermark lifting and visualization device with a phenol red indicator.

A finger was applied to a hardwound brown janitorial paper towel, printer paper and semi-glossy paper to deposit a fingermark onto each substrate. The fingermark lifting and visualization device was then applied to the substrates no later than 18 minutes after the ethanol wash. While wearing gloves, a user applied pressure directly on top of the fingermarks by pressing down on the PVDF for 10 seconds. The device was able to lift and visualize the fingermarks with good ridge detail. The fingermarks were visible long enough to permit the taking of photographs with a standard NIKON® DSLR camera under ambient light. FIG. 20 is a photograph of the fingermark that was lifted and visualized from the hardwound brown janitorial paper towel. FIG. 21 is a photograph of the fingermark that was lifted and visualized from the printer paper. FIG. 22 is a photograph of the fingermark that was lifted and visualized from the semi-glossy paper.

These results demonstrate that the fingermark lifting and visualization device is capable of lifting and visualizing fingermarks from a variety of substrates, including glossy papers.

REFERENCES

1. "Fingerprint", available online at en.wikipedia.org/Fingerprint (Oct. 1, 2017).
2. "Fingerprint powder", available online at en.wikipedia.org/Fingerprint_powder (Oct. 17, 2017).
3. Sodhi, G. S. et al., "Physical developer method for detection of latent fingerprints: a review", Egyptian Journal of Forensic Sciences, Vol. 6, pp. 44-47 (2016).
4. "Processing guide for developing latent prints", U.S. Department of Justice Federal Bureau of Investigation (2000).
5. "Gelatin lifters", BVDA International, available online at www.bvda.com/EN/download/en_gellifters.pdf (accessed on Nov. 13, 2017).
6. "Method for fingerprint identification", Interpol European Expert Group on Fingerprint Identification (2006).
7. International Fingerprint Research Group, "Guidelines for the assessment of fingermark detection techniques", Journal of Forensic Identification, Vol. 64, No. 2, pp. 174-200 (2014).
8. "What is Zar-Pro?", available online at www.zar-pro.com, 2010.
9. Almog, J. et al., "Aminoninhydrins: fingerprint reagents with direct fluorogenic activity—preliminary studies", Journal of Forensic Sciences, Vol. 36, pp. 104-110 (1991).
10. Urano, Y. et al., "Selective molecular imaging of viable cancer cells with pH-activatable fluorescence probes", Nature Medicine, Vol. 15, pp. 104-109 (2009).
11. Tahtouh, M. et al., "The detection and enhancement of latent fingermarks using infrared chemical imaging," *Journal of Forensic Sciences*, Vol. 50, No. 1, pp. JFS2004213-9 (2005).
12. Wood, M. et al., "Visualization of latent fingermarks using an aptamer-based reagent", Angewandte Chemie International Edition, Vol. 51, pp. 12272-12274 (2012).
13. Worley, C. G. et al., "Detection of visible and latent fingerprints using micro-X-ray fluorescence elemental imaging", Journal of Forensic Sciences, Vol. 51, pp. 57-63 (2006).
14. Dilag, J. et al., "Cadmium sulfide quantum dot/chitosan nanocomposites for latent fingermark detection", Forensic Science International, Vol. 187, No. 1-3, pp. 97-102 (2009).
15. Wiesner, S. et al., "Chemical development of latent fingerprints: 1,2-indanedione has come of age," Journal of Forensic Sciences, Vol. 46, No. 5, pp. 1082-1084 (2001).
16. Crane, N. J. et al., "Infrared spectroscopic imaging for noninvasive detection of latent fingerprints", Journal of Forensic Sciences, Vol. 52, pp. 48-53 (2007).
17. Park, D-H. et al., "Hydrochromic approaches to mapping human sweat pores", Accounts of Chemical Research, Vol. 49, No. 6, pp. 1211-1222 (2016).
18. van Dam, A. et al., "The compatibility of fingerprint visualization techniques with immunolabeling", Journal of Forensic Sciences, Vol. 58, pp. 999-1002 (2013).
19. Wu, P. et al., "Dual-emitting quantum dot nanohybrid for imaging of latent fingerprints: simultaneous identification of individuals and traffic light-type visualization of TNT", Chemical Science, Vol. 6, pp. 4445-4450 (2015).
20. Chinese Patent Application Publication No. CN106596482.
21. Chinese Patent Application Publication No. CN106248647.
22. Chinese Patent Application Publication No. CN105411599.
23. U.S. Patent Application Publication No. 2011/104815.
24. Chinese Patent Application Publication No. CN103431867.
25. U.S. Patent Application Publication No. 2010/310755.
26. U.S. Patent Application Publication No. 2010/047433.
27. Chinese Patent Application Publication No. CN101308061.
28. U.S. Patent Application Publication No. 2008/0136159.
29. U.S. Patent Application Publication No. 2010/0040765.
30. U.S. Patent Application Publication No. 2010/0136208.
31. Champod, C. et al., "Fingerprints and other ridge skin impressions", CRC Press, Boca Raton, Fla. (2016).
32. Ma, R. et al., "Fingermark detection on non-porous and semi-porous surfaces using $YVO_4$:Er,Yb luminescent upconverting particles", Forensic Science International Vol. 217, pp. e23-e26 (2012).
33. Chadwick, S. et al., "Styryl dye coated metal oxide powders for the detection of latent fingermarks on non-porous surfaces", Forensic Science International, Vol. 219, pp. 208-214 (2012).
34. Moret, S. "Application de nanoparticules luminescentes pour la detection de traces papillaires" Doctoral Thesis, University of Lausanne (2013).
35. Tahtouh, M. et al., "The application of infrared chemical imaging to the detection and enhancement of latent fingerprints: Method optimization and further findings", Journal of Forensic Sciences, Vol. 52, pp. 1089-1096 (2007).
36. Wilkinson, D., "A one-step fluorescent detection method for lipid fingerprints; $Eu(TTA)_3$.2TOPO", Forensic Science International, Vol. 99, pp. 5-23 (1999).
37. Jaber, N. et al., "Visualization of latent fingermarks by nanotechnology: Reversed development on paper—A remedy to the variation in sweat composition", Angewandte Chemie International Edition, Vol. 51, pp. 12224-12227 (2012).
38. Kent, T., "Standardizing protocols for fingerprint reagent testing", Journal of Forensic Identification, Vol. 60, pp. 371-379 (2010).
39. Wiesner, S. et al., "Lifting bloody footwear impressions using alginate casts followed by chemical enhancement", Journal of Forensic Sciences, Vol. 58, pp. 782-788 (2013).

40. Horvath, D., "Evaluation of alginate casting material for the lifting of latent and bloody fingermarks from various surfaces", Master of Science Thesis, University of Technology Sydney (2014).

41. Theeuwen, A. et al., "Enhancement of footwear impressions in blood", Forensic Science International, Vol. 95, pp. 133-151 (1998).

42. Farrugia, K. et al., "A Comparison of enhancement techniques for footwear impressions on dark and patterned fabric", Journal of Forensic Sciences, Vol. 58, pp. 1472-1485 (2013).

43. Munro, M. et al., "A preliminary investigation into the use of alginates for the lifting and enhancement of fingermarks in blood", Science and Justice, Vol. 54, pp. 185-191 (2014).

44. Yang, R. et al., "Studies on the development of latent fingerprints by the method of solid medium ninhydrin", Forensic Science International, Vol. 242, pp. 123-126 (2014).

45. Zarate, J. et al., "A fluorogenic method for lifting, enhancing, and preserving bloody impression evidence", Journal of Forensic Identification, Vol. 61, pp. 260-280 (2011).

46. Becue, A., "Emerging fields in fingermark (meta) detection—A critical review", Analytical Methods, Vol. 8, pp. 7983-8003 (2016).

47. Spindler, X. et al., "Enhancement of latent fingermarks on non-porous surfaces using anti-L-amino acid antibodies conjugated to gold nanoparticles", Chemical Communications, Vol. 47, pp. 5602-5604 (2011).

48. Ramotowski, R. S., "Composition of latent print residue", Advances in Fingerprint Technology, 2nd ed., Chapter 3; CRC Press, Boca Raton, FL (2001).

49. Kaiser, D. et al., "Hydrogen ion and electrolyte excretion of the single human sweat gland", Pflügers Archiv—European Journal of Physiology, Vol. 349, pp. 63-72 (1974).

50. Kaiser, D. et al., "Diminished excretion of bicarbonate from the single sweat gland of patients with cystic fibrosis of the pancreas", European Journal of Clinical Investigation, Vnl 4, pp, 261-265 (1974).

51. Curto, V. F. et al., "Concept and development of an autonomous wearable micro-fluidic platform for real time pH sweat analysis", Sensors and Actuators B-Chemical, Vol. 175, pp. 263-270 (2012).

52. Neupert, M., "Lackmus", Römpp Lexikon Chemie, available online at www.chemeurope.com/en/encyclopedia/Litmus_test_%28chemistry%29.html (2013).

53. Bamfield, P., "Chromic phenomena: The technological applications of colour chemistry", The Royal Society of Chemistry, Cambridge, UK, p. 41 (2001).

54. Williams, A. et al., "Carbodiimide chemistry: Recent advances", Chemical Reviews, Vol. 81, pp. 589-636 (1981).

55. Hermanson, G. T., "Bioconjugate chemistry", 3rd ed., Elsevier, Amsterdam pp. 237-238, 246-248 (2013).

56. Han, J. et al., "Fluorescent indicators for intracellular pH", Chemical Reviews, Vol. 110, pp. 2709-2728 (2010).

57. "LysoTracker and LysoSensor Probes", Molecular Probes by life technologies, available online at tools.thermofisher.com/content/sfs/manuals/mp07525.pdf (2013).

58. "pHrodo Indicators for pH Determination", ThermoFisher Scientific, available online at www.thermofisher.com/us/en/home/brands/molecular-probes/key-molecular-probes-products/phrodo-indicators.html (accessed on Jan. 5, 2018).

59. Galindo, F. et al., "Synthetic macrocyclic peptidomimetics as tunable pH probes for the fluorescence imaging of acidic organelles in live cells", Angewandte Chemie International Edition, Vol. 44, pp. 6504-6508 (2005).

60. Werner, T. et al., "Novel optical pH-sensor based on a boradiaza-indacene derivative", Fresenius Journal of Analytical Chemistry, Vol. 359, pp. 150-154 (1997).

61. Yogo, T. et al., "Selective photoinactivation of protein function through environment-sensitive switching of singlet oxygen generation by photosensitizer", Proceedings of the National Academy of Sciences of the United States of America, Vol. 105, pp. 28-32 (2008).

62. Xiong, H. et al., "Activatable water-soluble probes enhance tumor imaging by responding to dysregulated pH and exhibiting high tumor-to-liver fluorescence emission contrast", Bioconjugate Chemistry, Vol. 27, pp. 1737-1744 (2016).

63. Liappis, N. et al., "The trace amino acid pattern in human eccrine sweat", Clinica Chimica Acta, Vol. 48, pp. 233-236 (1973).

64. Liappis, N. et al., "Quantitative study of free amino acids in human eccrine sweat excreted from the forearms of healthy trained and untrained men during exercise", European Journal of Applied Physiology, Vol. 42, pp. 227-234 (1979).

65. Emden, G. M. et al., "Ober das Vorkommen von Serin im menschlichen Schweiße", Biochemische Zeitschrift, Vol. 28, pp. 230-236 (1910).

66. Odén, S. et al., "Detection of fingerprints by the ninhydrin reaction", Nature, Vol. 173, pp. 449-450 (1954).

67. Yamashita, B. et al., "Latent print development" The fingerprint sourcebook, Chapter 7, National Institute of Justice, Washington, D.C. (2011).

68. Ramotowski, R. S., "Amino acid reagents", Lee and Gaensslen's Advances in fingerprint technology, 3rd ed., Chapter 2, CRC Press, Boca Raton, Fla. (2013).

69. Hansen, D. B et al., "The development of novel ninhydrin analogues", Chemical Society Reviews, Vol. 34, pp. 408-417 (2005).

70. Hark, R. R. et al., "Synthetic studies of novel ninhydrin analogs", Canadian Journal of Chemistry, Vol. 79, pp. 1632-1654 (2001).

71. Hark, R. R., "Synthesis of ninhydrin analogues", Ph.D. Dissertation, University of Pennsylvania (1996).

72. Ziarani, G. M. et al., "Ninhydrin in synthesis of heterocyclic compounds", ARKIVOC, Vol. vi, pp. 1-139 (2015).

73. Regitz, R., "Diazo compounds", Chapter 3, Elsevier, Amsterdam (1986).

74. National Research Council, "Strengthening forensic science in the United States: A path forward", National Academies Press, Washington, D.C. (2009).

75. Pollanen, M. S. et al., "Forensic science in Canada", University of Toronto Hart House Report (2012).

76. Mnookin, J. L. et al., "The need for a research culture in the forensic science", UCLA Law Review, Vol. 58, pp. 725-780 (2010-2011).

77. Hofstetter, O. et al., "Chiral Discrimination Using an lmmunosensor", Nature Biotechnology, Vol. 17, pp. 371-374 (1999).

78. Kassa, T. et al., "Antibody-based multiplex analysis of structurally closely related chiral molecules", Analyst, Vol. 136, pp. 1113-1115 (2011).

79. Tsourkas, A. et al., "Magnetic relaxation switch immunosensors detect enantiomeric impurities", Angewandte Chemie International Edition, Vol. 43, pp. 2395-2399 (2004).

80. Dutta, P. et al., "Enantioselective sensors based on antibody-mediated nanomechanics", Analytical Chemistry, Vol. 75, pp. 2342-2348 (2003).

What is claimed is:

1. A fingermark lifting and visualization device, comprising:
   a carrier having a lifting surface, and
   an indicator, immobilized on the lifting surface,
   wherein the indicator changes color or changes in fluorescence in the visible spectrum in response to contact with a glandular secretion in an invisible fingermark, to lift and visualize the fingermark without a developer or further treatment,
   the device passes the fingermark point test,
   the device passes the basic visualization test,
   the device passes the basic contact time test, and
   the device passes the basic stability test.

2. The fingermark lifting and visualization device of claim 1, wherein the carrier comprises positively charged nylon or polyvinylidene fluoride (PVDF).

3. The fingermark lifting and visualization device of claim 1, wherein the indicator comprises a pH-sensitive substance or an amine-reactive substance.

4. The fingermark lifting and visualization device of claim 1, wherein the indicator comprises an amine-reactive substance selected from the group consisting of ninhydrin and ninhydrin derivatives, amido black, 1,8-diazafluoren-9-one (DFO), 1,2-indanedione, p-dimethylaminocinnamaldehyde (pDMAC), 4-chloro-7-nitrobenzofurazan (NBD chloride), dansyl chloride, o-phthalaldehyde (OPA), fluorescamine, genipin, and lawsone.

5. The fingermark lifting and visualization device of claim 1, wherein the indicator comprises a pH-sensitive substance selected from the group consisting of phthalides, triarylmethanes, fluorans, azo-dyes, styryl-dyes, and indophenols.

6. The fingermark lifting and visualization device of claim 1, wherein the indicator comprises a pH-sensitive substance selected from the group consisting of bromophenol red, phenol red, bromocresol purple, Congo red, methyl red, neutral red, bromoxylenol blue, bromothymol blue, bromocresol green, boron-dipyrromethene (BODIPY), Green DND-26, 1,3,5,7-tetramethyl-8-(4-dimethyl-amino)-4-difluoroboroa-3a,4a-diaza-(s)-indacene, N,N-dimethylaminophenyl-2,6-dicarboxyethyl-1,3,5,7-tetramethylboron-dipyrromethene (DiMeNBDP), $H_2$NBDP, EtMeNBDP, and DiEtNBDP and PhBDP.

7. The fingermark lifting and visualization device of claim 1, wherein the indicator comprises a polymer doped with a pH-sensitive substance.

8. The fingermark lifting and visualization device of claim 1, wherein the device passes at least one test selected from the group consisting of the enhanced visualization test, the fingermark point test, the enhanced contact time test, and the enhanced stability test.

9. The fingermark lifting and visualization device of claim 1, wherein the pH of the indicator has been adjusted to be less than 4 or greater than 7.

10. The fingermark lifting and visualization device of claim 1 wherein the indicator comprises phenol red, and
    the pH of the indicator has been adjusted to be greater than 7.

11. A method of making the fingermark lifting and visualization device of claim 1, comprising:
    creating an indicator solution, comprising the indicator and a solvent;
    applying the indicator solution to the lifting surface of the carrier to form an impregnated carrier;
    incubating the impregnated carrier; and
    drying the impregnated carrier.

12. A method of visualizing a fingermark on a substrate, comprising:
    contacting the fingermark lifting and visualization device of claim 1 with the fingermark on the substrate;
    wherein the fingermark is an undeveloped fingermark.

13. The method of claim 12, wherein the method comprises neither powdering nor cyanoacrylate fuming.

14. The method of claim 12, wherein the substrate is reflective, patterned, luminescent, reactive, textured, and/or porous.

15. A fingermark lifting and visualization device, comprising:
    a carrier having a lifting surface, and
    an indicator, immobilized on the lifting surface,
    wherein the carrier comprises a polymer selected from the group consisting of positively charged nylon, nylon, and polyvinylidene fluoride (PVDF),
    the indicator comprises a pH-sensitive substance,
    the pH of the indicator has been adjusted to be basic, and
    the indicator changes color or changes in fluorescence in the visible spectrum in response to contact with a glandular secretion in an invisible fingermark, to lift and visualize the fingermark without a developer or further treatment.

16. The fingermark lifting and visualization device of claim 15, wherein the pH-sensitive substance is selected from the group consisting of phenol red, phenol red-doped agarose, bromocresol purple, bromocresol purple-doped agarose, and N,N-dimethylaminophenyl-2,6-dicarboxyethyl-1,3,5,7-tetramethylboron-dipyrromethene (DiMeNBDP).

17. The fingermark lifting and visualization device of claim 16, wherein the indicator further comprises a polymer.

18. A fingermark lifting and visualization device, comprising:
    a carrier having a lifting surface, and
    an indicator, immobilized on the lifting surface,
    wherein the carrier comprises a polymer selected from the group consisting of positively charged nylon, nylon, and polyvinylidene fluoride (PVDF),
    the indicator comprises an amine-reactive substance, and
    the indicator changes color or changes in fluorescence in the visible spectrum in response to contact with a glandular secretion in an invisible fingermark, to lift and visualize the fingermark without a developer or further treatment.

19. The fingermark lifting and visualization device of claim 18, wherein the amine-reactive substance comprises ninhydrin or fluorescamine.

20. The fingermark lifting and visualization device of claim 18, wherein the indicator further comprises a polymer.

21. The method of claim 12, further comprising exposing the device to an ultraviolet light source after the contacting to visualize the fingermark on the indicator.

22. A method of visualizing a fingermark on a substrate, comprising:
    contacting the fingermark lifting and visualization device of claim 15 with the fingermark on the substrate;
    wherein the fingermark is an undeveloped fingermark.

23. The method of claim 22, further comprising exposing the device to an ultraviolet light source after the contacting to visualize the fingermark on the indicator.

24. The fingermark lifting and visualization device of claim 7, wherein the polymer is selected from the group consisting of gelatin, agarose, and dextran.

25. The fingermark lifting and visualization device of claim 17, wherein the polymer is selected from the group consisting of gelatin, agarose, and dextran.

26. The fingermark lifting and visualization device of claim 20, wherein the polymer is selected from the group consisting of gelatin, agarose, and dextran.

27. The fingermark lifting and visualization device of claim 1, further comprising a cover, on the indicator.

28. The fingermark lifting and visualization device of claim 15, further comprising a cover, on the indicator.

29. The fingermark lifting and visualization device of claim 18, further comprising a cover, on the indicator.

30. The fingermark lifting and visualization device of claim 1, further comprising a cover, on the indicator,
   wherein the carrier comprises positively charged nylon or polyvinylidene fluoride (PVDF),
   the indicator comprises a pH-sensitive substance,
   the pH of the indicator has been adjusted to be less than 4 or greater than 7,
   the indicator further comprises a polymer, and
   the polymer is selected from the group consisting of gelatin, agarose, and dextran.

\* \* \* \* \*

UNITED STATES PATENT AND TRADEMARK OFFICE
CERTIFICATE OF CORRECTION

PATENT NO. : 10,866,188 B2  
APPLICATION NO. : 15/945142  
DATED : December 15, 2020  
INVENTOR(S) : Oliver D. Hofstetter et al.

Page 1 of 1

It is certified that error appears in the above-identified patent and that said Letters Patent is hereby corrected as shown below:

On the Title Page

After Assignee: Board of Trustees of Northern Illinois University
 DeKalb, IL (US)

Please insert the following two (2) Assignees:
--Western Sydney University
Werrington NSW, (AU)
University of Technology Sydney
Ultimo, (AU)--

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*